United States Patent
Jahangir et al.

(10) Patent No.: US 12,409,311 B2
(45) Date of Patent: Sep. 9, 2025

(54) MOTOR CABLES FOR INTRAVASCULAR BLOOD PUMPS

(71) Applicant: ABIOMED, Inc., Danvers, MA (US)

(72) Inventors: Emilia Jahangir, Danvers, MA (US); Qingchao Kong, Danvers, MA (US); Martin Kortyka, Aachen (DE)

(73) Assignee: ABIOMED, INC., Danvers, MA (US)

( * ) Notice: Subject to any disclaimer, the term of this patent is extended or adjusted under 35 U.S.C. 154(b) by 355 days.

(21) Appl. No.: 17/884,903

(22) Filed: Aug. 10, 2022

(65) Prior Publication Data
US 2023/0051950 A1   Feb. 16, 2023

Related U.S. Application Data

(60) Provisional application No. 63/232,323, filed on Aug. 12, 2021.

(51) Int. Cl.
*A61M 60/148* (2021.01)
*A61M 60/13* (2021.01)
*A61M 60/422* (2021.01)

(52) U.S. Cl.
CPC ........ *A61M 60/148* (2021.01); *A61M 60/422* (2021.01); *A61M 60/13* (2021.01)

(58) Field of Classification Search
CPC .. A61M 60/148; A61M 60/422; A61M 60/13; A61M 60/221; A61M 60/416; A61M 60/878
See application file for complete search history.

(56) References Cited

U.S. PATENT DOCUMENTS

| 9,550,017 B2 | 1/2017 | Spanier et al. |
| 2007/0273221 A1* | 11/2007 | Kinoshita ................ H02K 3/50 |
| | | 310/58 |
| 2021/0015982 A1* | 1/2021 | Kerkhoffs ........... A61M 60/416 |

FOREIGN PATENT DOCUMENTS

| AU | 2019283407 A1 | 1/2021 |
| EP | 3542835 A1 | 9/2019 |
| WO | 2019234146 A1 | 12/2019 |

OTHER PUBLICATIONS

International Search Report and Written Opinion for Application No. PCT/US2022/039947 dated Nov. 28, 2022 (12 pages).
Written Opinion issued in corresponding Singapore Patent Application No. 11202400511Y mailed on Jan. 10, 2025, 6 pages.

* cited by examiner

*Primary Examiner* — Mark W. Bockelman
(74) *Attorney, Agent, or Firm* — Botos Churchill IP Law LLP

(57) ABSTRACT

Systems and methods for providing hemodynamic support to a patient with an intravascular blood pump are disclosed. In some implementations, the blood pump includes a motor and an improved motor cable for delivering electrical power to the motor. The motor includes a stator with one or more coils. The motor cable includes one or more electrical conduits. The motor cable also includes a tail portion and a head portion. In some implementations, the head portion may have an O-shape or a C-shape. The motor cable may reduce the complexity of assembling the blood pump. For example, the motor cable may reduce the risk of shorting the one or more coils and/or the one or more electrical conduits.

20 Claims, 16 Drawing Sheets

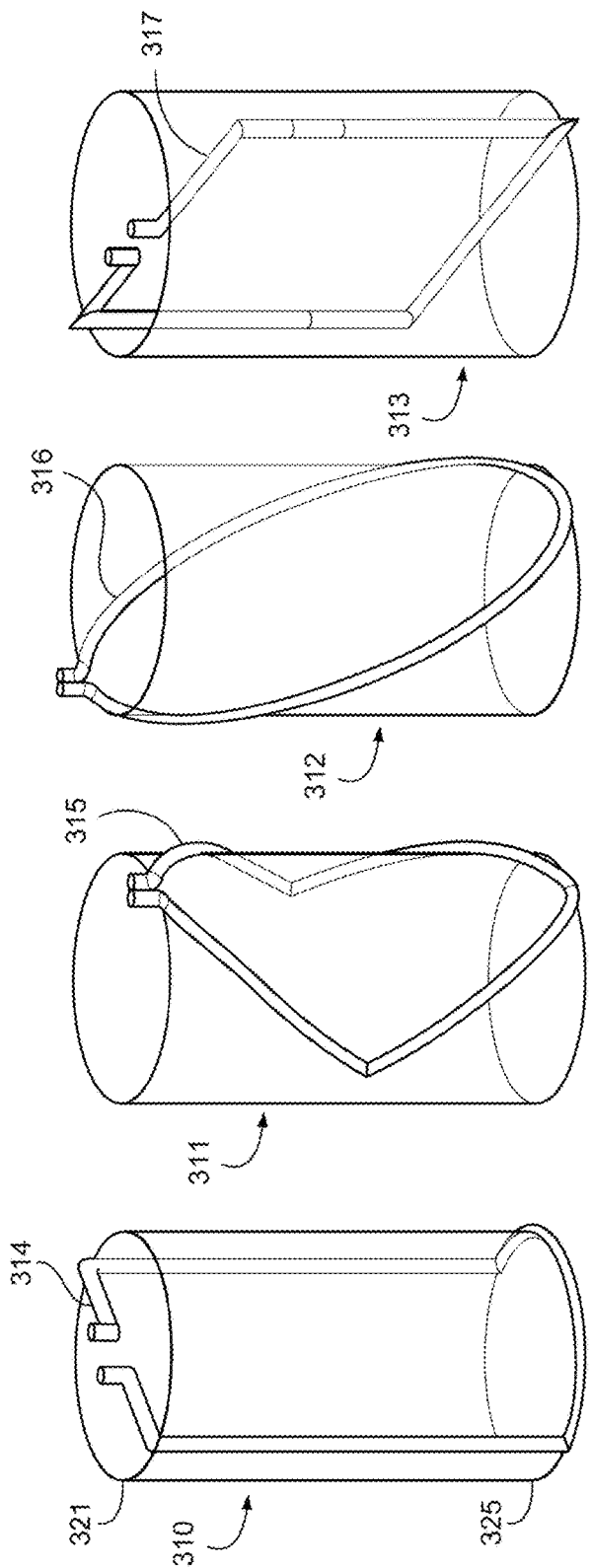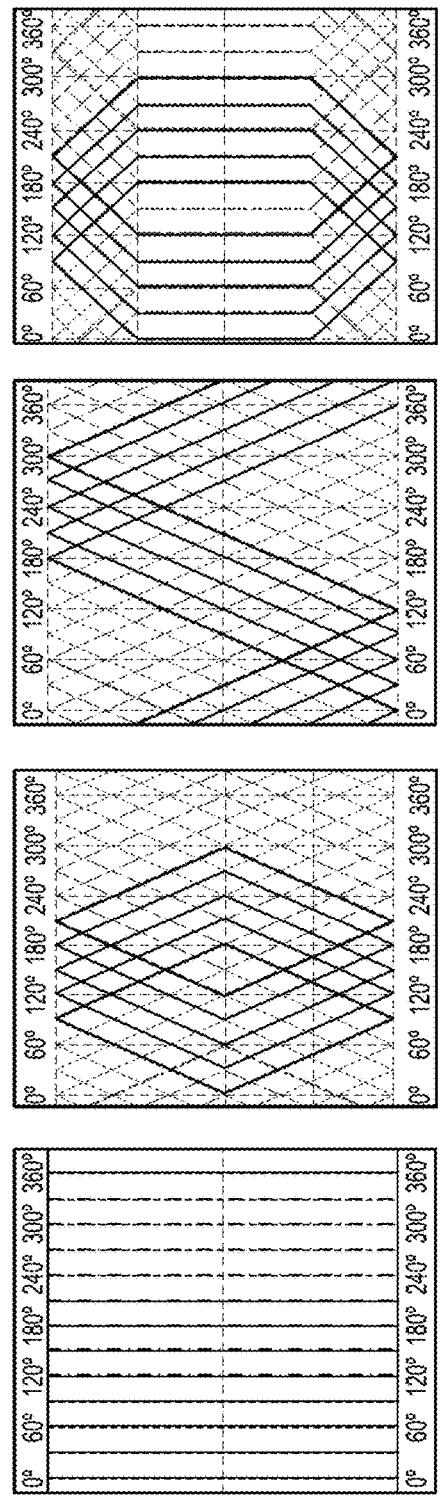

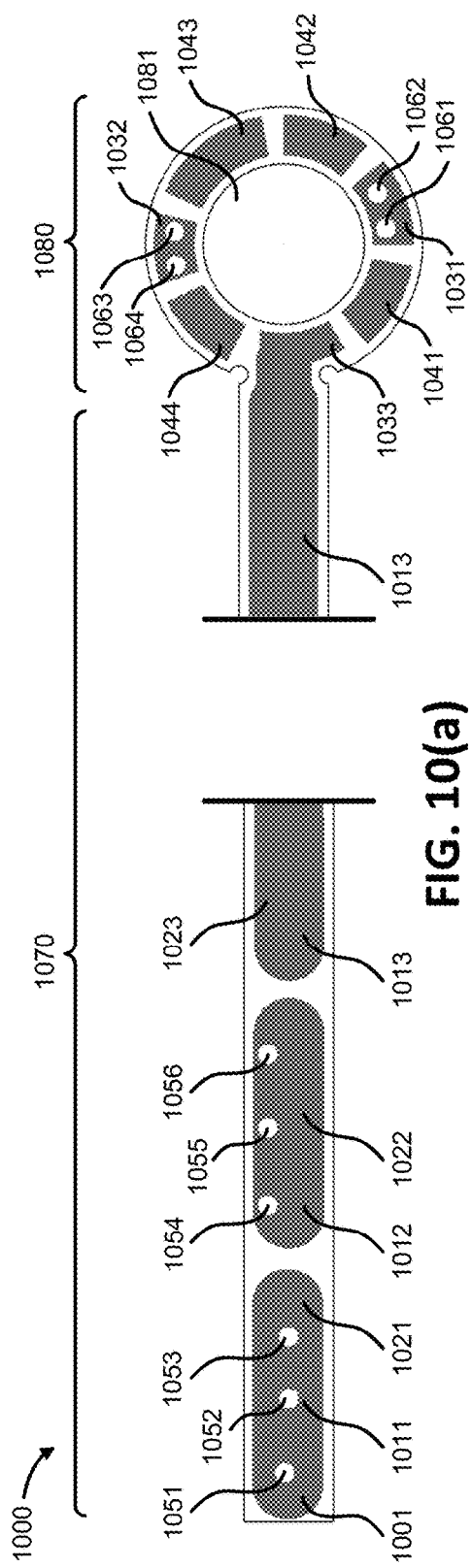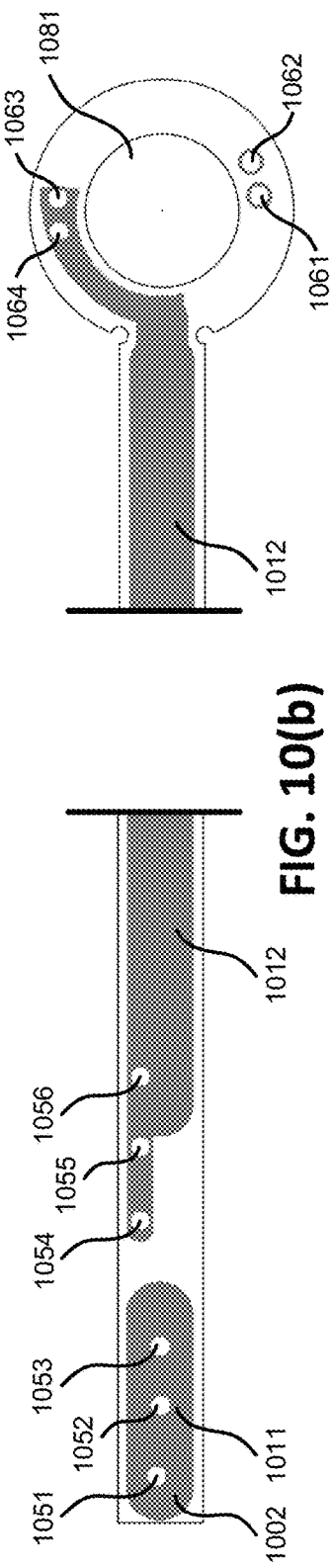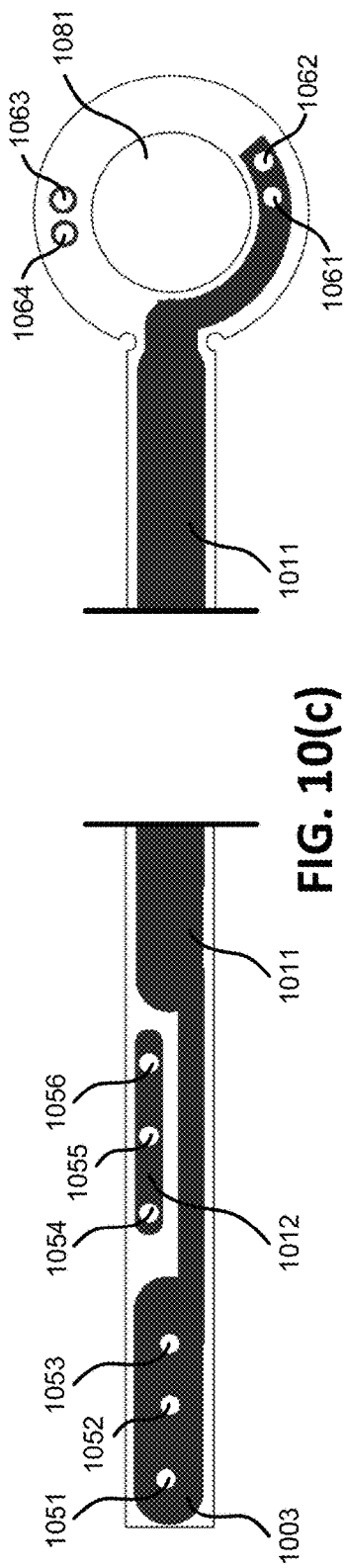
FIG. 10(a)
FIG. 10(b)
FIG. 10(c)

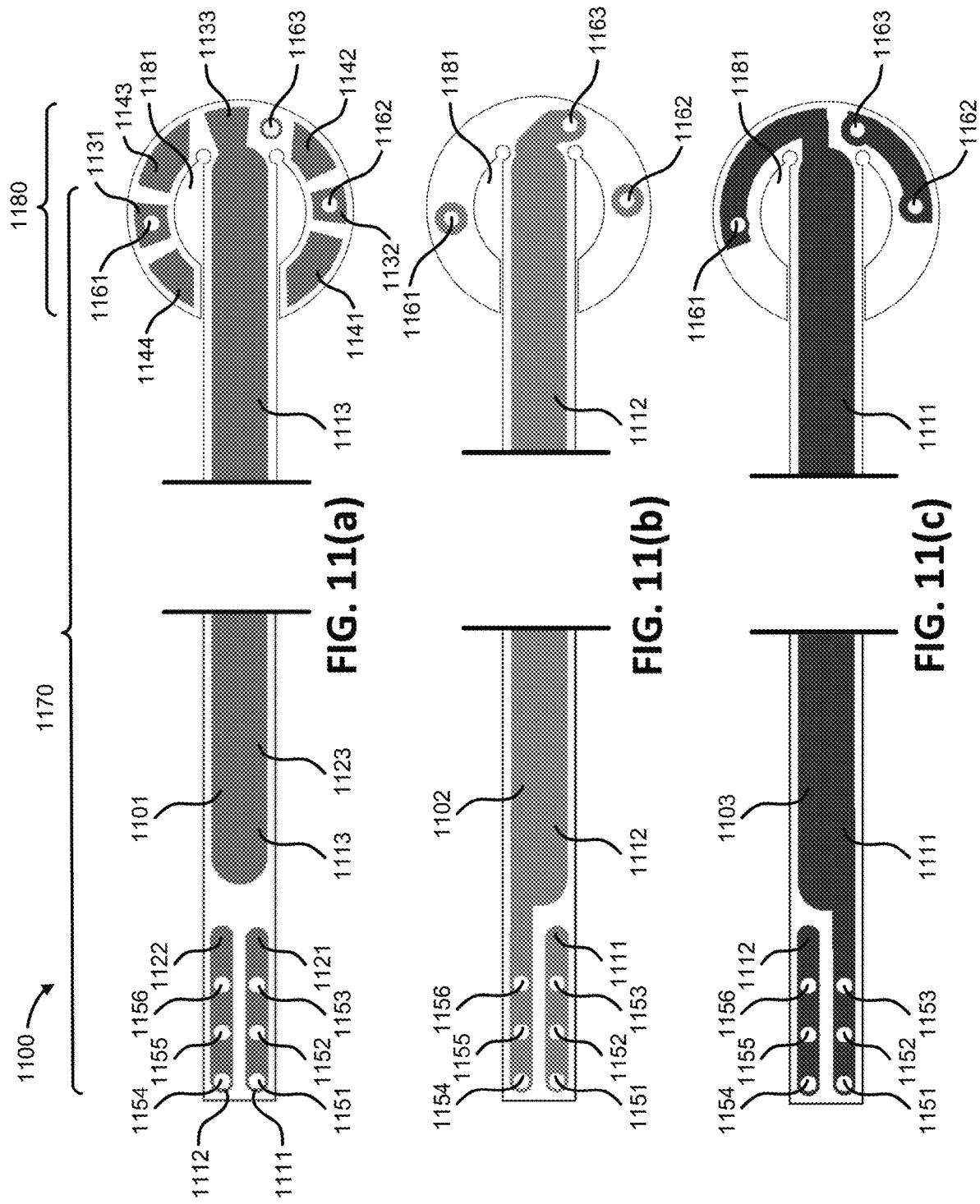

MOTOR CABLES FOR INTRAVASCULAR BLOOD PUMPS

CROSS-REFERENCE TO RELATED APPLICATIONS

This application claims priority from and the benefit of U.S. Provisional Application No. 63/232,323, which was filed on Aug. 12, 2021, and is incorporated by reference herein.

TECHNICAL FIELD

The present technology relates to systems and methods for providing hemodynamic support to a patient with an intravascular blood pump. In some implementations, the blood pump includes a motor and an improved motor cable for delivering electrical power to the motor.

BACKGROUND

An intravascular blood pump may be inserted into a patient's blood vessel (e.g., the aorta) by means of a catheter to provide hemodynamic support. An intravascular blood pump may include an inlet area, an outlet area, a cannula, and a motor housing. During operation, blood may be drawn into one or more openings of the inlet area, channeled through the cannula, and expelled through one or more openings of the outlet area by a motor disposed within the motor housing. Failure of the motor may cause serious problems for a patient. Furthermore, even if the motor can be replaced after the blood pump has been inserted in the patient, such a replacement imposes additional risks on the patient.

BRIEF SUMMARY

Systems and methods for providing hemodynamic support to a patient with an intravascular blood pump are disclosed. In some implementations, the blood pump includes a motor and an improved motor cable for delivering electrical power to the motor. The motor includes a stator with one or more coils. The motor cable includes one or more electrical conduits. The motor cable also includes a tail portion and a head portion. In some implementations, the head portion may have an O-shape or a C-shape. The motor cable may reduce the complexity of assembling the blood pump. For example, the motor cable may reduce the risk of shorting the one or more coils and/or the one or more electrical conduits.

One aspect of the present disclosure relates to an intravascular blood pump comprising an inlet area having one or more openings, an outlet area having one or more openings, a passage fluidically coupling the inlet and outlet areas, a motor having a rotor and a stator, and a cable having a tail portion and a head portion. The stator of the motor includes one or more coils and is configured to generate a rotating magnetic field in response to receiving one or more electrical signals at the one or more coils. The rotating magnetic field causes the rotor to rotate. Rotation of the rotor draws blood into the one or more openings of the inlet area, channels the blood through the passage, and expels the blood through the one or more openings of the outlet area. One or more electrical conduits extend through the tail and head portions of the cable. The head portion of the cable includes one or more pads. At least one of the coils of the stator of the motor is coupled to at least one of the electrical conduits of the cable through at least one of the pads of the head portion of the cable.

In some implementations, the stator has an even number of coils. In some implementations, the one or more coils and the one or more electrical conduits are coupled to the one or more pads to form a star circuit configuration. In some implementations, the one or more coils and the one or more electrical conduits are coupled to the one or more pads to form a delta circuit configuration. In some implementations, the one or more coils and the one or more electrical conduits are coupled to the one or more pads to form an open end windings circuit configuration.

In some implementations, the head portion of the cable is coupled to a yoke of the motor. In some implementations, the head portion of the cable is coupled to a bearing or a bushing. In some implementations, a shaft extends through (a) an opening of the bearing or the bushing and (b) an opening of the head portion of the cable. In some implementations, the head portion of the cable is O-shaped. In some implementations, the head portion of the cable is C-shaped. In some implementations, the cable is bent near an interface between the tail portion and the head portion at an angle between 45 and 135 degrees.

In some implementations, at least one of the electrical conduits includes a plurality of electrically conductive layers and a plurality of through holes, wherein each of the conductive layers is separated by at least one electrically insulating layer. In some implementations, the head portion of the cable includes an adhesive layer beneath the plurality of conductive layers. In some implementations, the tail portion includes a coating covering sections of the plurality of electrically conductive layers. In some implementations, the tail portion includes one or more pads. In such implementations, the one or more pads of the tail portion and the one or more pads of the head portion may be exposed.

Another aspect of the present disclosure relates to a method for assembling an intravascular blood pump comprising a motor and a cable. The motor includes a rotor and a stator having one or more coils. The stator is configured to generate a rotating magnetic field in response to receiving one or more electrical signals at the one or more coils. The rotating magnetic field causes the rotor to rotate. The cable includes a tail portion and a head portion having one or more pads. One or more electrical conduits extend through the tail and head portions of the cable. The method comprises coupling the head portion of the cable to an internal structure of the intravascular blood pump (e.g., a yoke, a bearing, or a bushing) and coupling at least one coil of the motor to at least one of the electrical conduits through at least one of the pads.

In some implementations, the head portion of the cable is O-shaped or C-shaped. In some implementations, at least one of the electrical conduits comprises a plurality of electrically conductive layers and a plurality of through holes. In such implementations, each of the conductive layers is separated by at least one electrically insulating layer. In some implementations, the head portion comprises an adhesive layer beneath the plurality of conductive layers, and coupling the head portion to the internal structure of the intravascular blood pump comprises placing the adhesive layer on the internal structure. In some implementations, coupling the at least one coil to the at least one of the electrical conduits through the at least one of the pads comprises soldering the at least one coil to the at least one of the pads.

BRIEF DESCRIPTION OF DRAWINGS

FIGS. 3(a)-(d) illustrate coil winding patterns for individual turns in a coil.

FIGS. 3(e)-(h) illustrate coil winding patterns formed by coils having the individual turns shown in FIGS. 3(a)-(d).

FIGS. 10(a)-(c) illustrate a top, middle, and bottom electrically conductive layer, respectively, of a motor cable.

FIGS. 11(a)-(c) illustrate a top, middle, and bottom electrically conductive layer, respectively, of a motor cable.

DETAILED DESCRIPTION

Figure 1B:
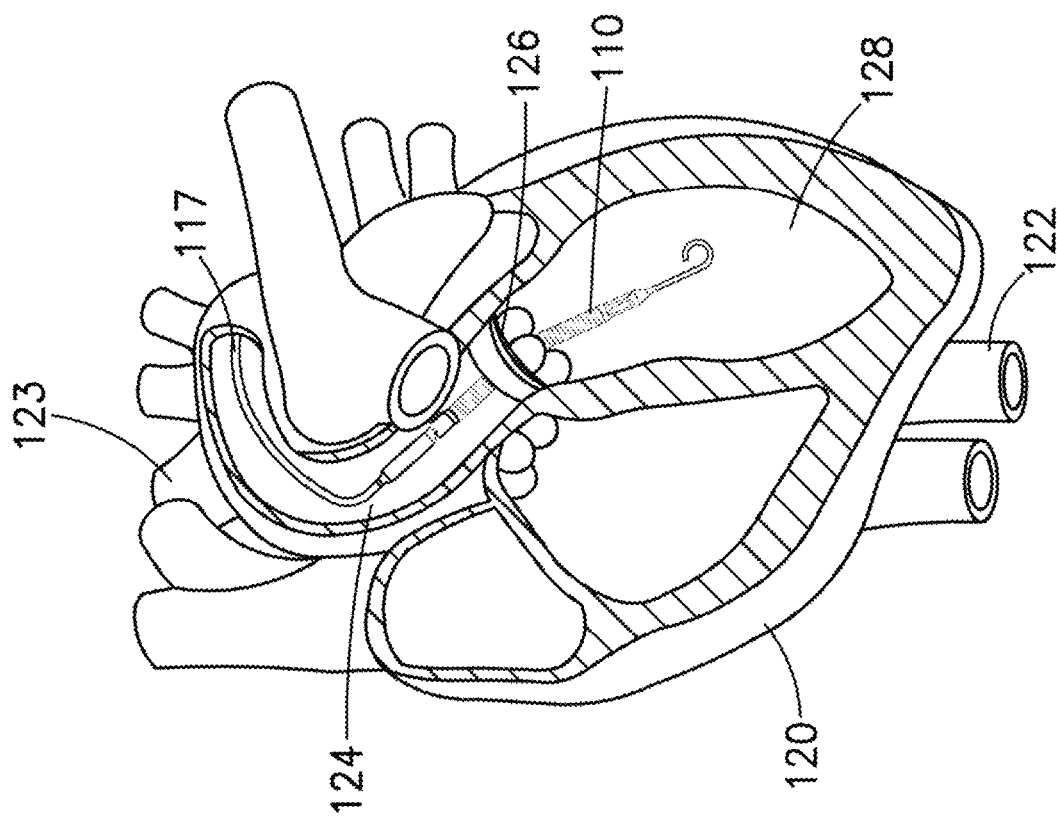
FIG. 1(b) illustrates the blood pump of FIG. 1(a) positioned within the heart of a patient.

Implementations of the present disclosure are described in detail with reference to the drawing figures wherein like reference numerals identify similar or identical elements. It is to be understood that the disclosed implementations are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

An intravascular blood pump is a percutaneous, catheter-based device that can be used to provide hemodynamic support to the heart of a patient (e.g., during a high-risk percutaneous coronary intervention). As shown in FIG. 1(a), an intravascular blood pump 110 may include a pigtail 111, an inlet area 112, a cannula 113, a pressure sensor 114, an outlet area 115, a motor housing 116, and/or a catheter 117. Pigtail 111 may assist with stabilizing blood pump 110 in the heart of a patient. During operation, blood may be drawn into one or more openings of inlet area 112, channeled through cannula 113, and expelled through one or more openings of outlet area 115 by a motor (not shown) disposed in motor housing 116. In some implementations, the blood flow inlet and outlet areas may be reversed, such that during operation, blood may be drawn into one or more openings of outlet area 115, channeled through cannula 113, and expelled through one or more openings of inlet area 112. In some implementations, pressure sensor 114 may include a flexible membrane that is integrated into cannula 113. One side of pressure sensor 114 may be exposed to the blood pressure on the outside of cannula 113, and the other side may be exposed to the pressure of the blood inside of cannula 113. In some such implementations, pressure sensor 114 may generate an electrical signal proportional to the difference between the pressure outside cannula 113 and the pressure inside cannula 113. In some implementations, a pressure difference measured by pressure sensor 114 may be used to position blood pump 110 within the heart of a patient. In some implementations, pressure sensor 114 is an optical pressure sensor. Catheter 117 may provide one or more fluidic and/or electrical connections between blood pump 110 and more or more other devices of a ventricular support system (see, e.g., FIG. 1(c)).

Figure 1A:
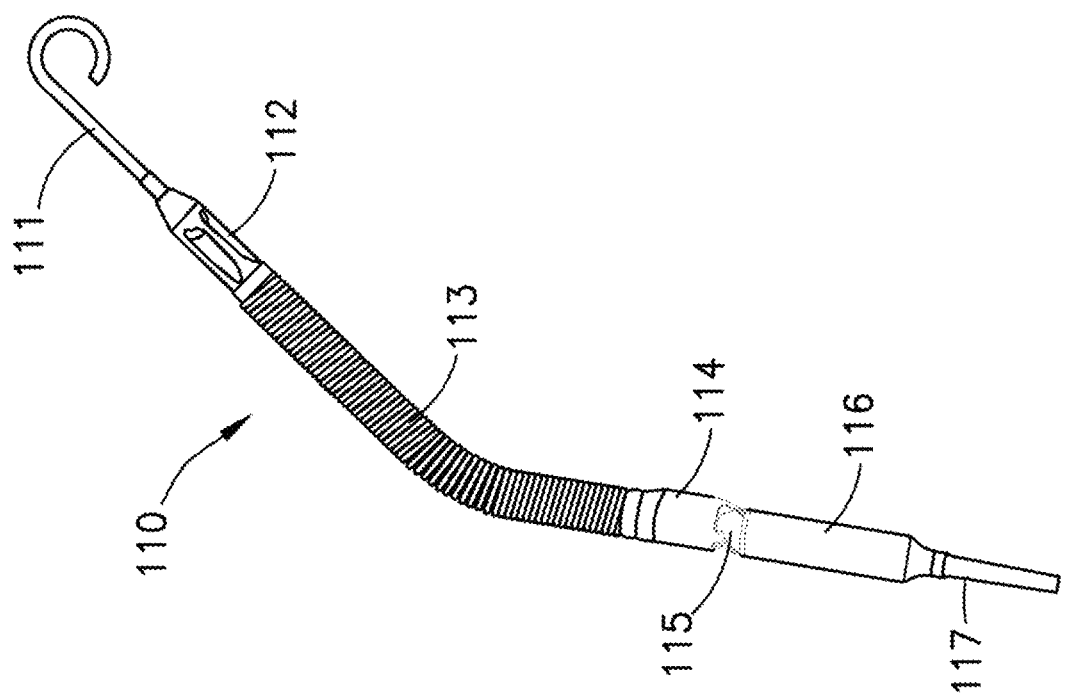
FIG. 1(a) illustrates an intravascular blood pump.

As shown in FIG. 1(b), blood pump 110 may be positioned in a patient's heart 120. As shown, blood pump 110 may, for example, be inserted percutaneously via the femoral artery 122 into the ascending aorta 124, across the aortic valve 126, and into the left ventricle 128. In other implementations, an intravascular blood pump may, for example, be inserted percutaneously via the axillary artery 123 into the ascending aorta 124, across the aortic valve 126, and into the left ventricle 128. In other implementations, an intravascular blood pump may, for example, be inserted directly into the ascending aorta 124, across the aortic valve 126, and into the left ventricle 128. During operation, blood pump 110 entrains blood from the left ventricle 128 and expels blood into the ascending aorta 124. As a result, blood pump 110 performs some of the work normally done by the patient's heart 120. The hemodynamic effects of blood pumps may include an increase in cardiac output, improvement in coronary blood flow resulting in a decrease in LV end-diastolic pressure, pulmonary capillary wedge pressure, myocardial workload, and oxygen consumption. In some implementations, blood pump 110 may be positioned within the right side of the heart and support the right sided circulation.

Figure 1C:
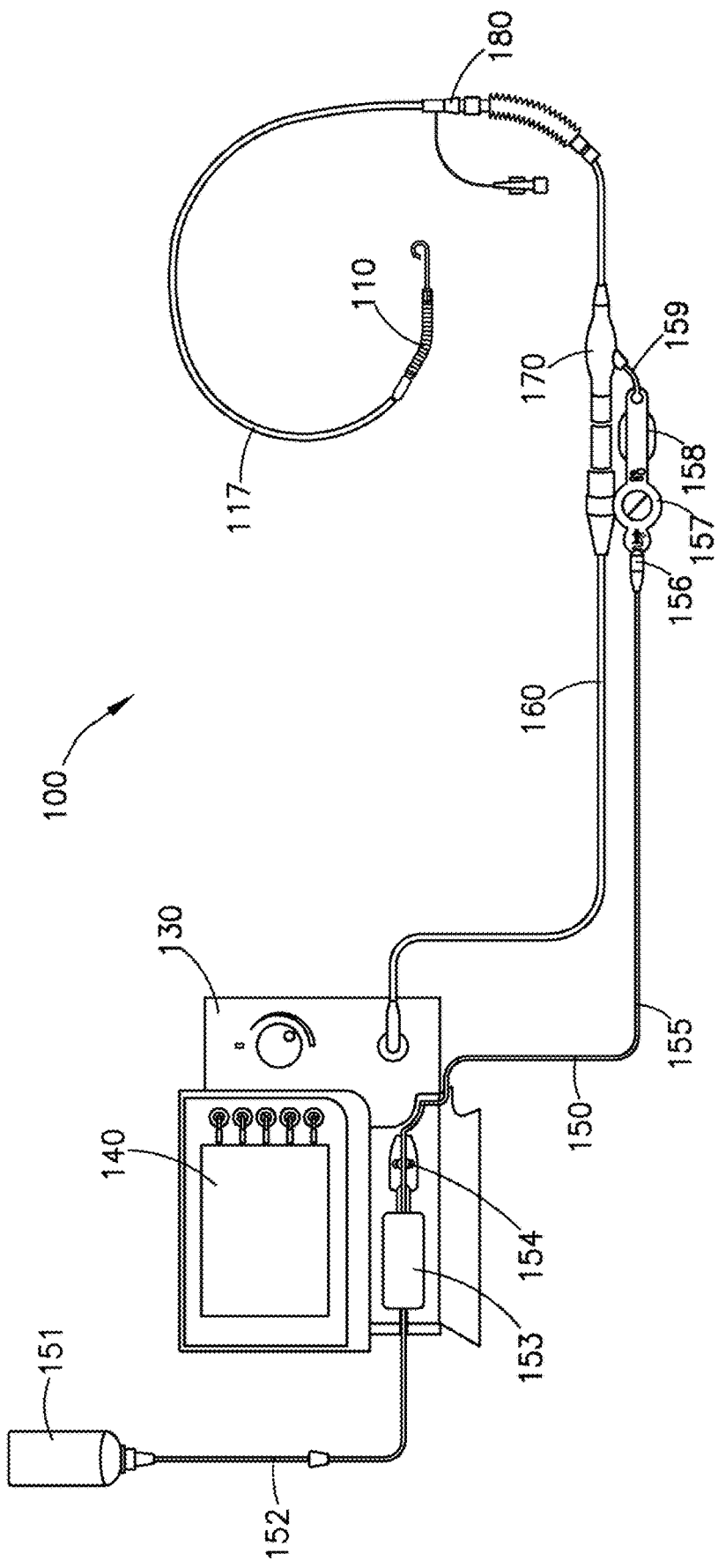
FIG. 1(c) illustrates a ventricular support system.

As shown in FIG. 1(c), blood pump 110 may be incorporated into a ventricular support system 100. Ventricular support system 100 also includes a controller 130 (e.g., an Automated Impella Controller® from Abiomed, Inc., Danvers, Mass.), a display 140, a purge subsystem 150, a connector cable 160, a plug 170, and a repositioning unit 180. As shown, controller 130 includes display 140. Controller 130 monitors and controls blood pump 110. During operation, purge subsystem 150 delivers a purge fluid to blood pump 110 through catheter 117 to prevent blood from entering the motor (not shown) within motor housing 116. In some implementations, the purge fluid is a dextrose solution (e.g., 5% dextrose in water with 25 or 50 IU/mL of heparin). Connector cable 160 provides an electrical and/or optical connection between blood pump 110 and controller 130. Plug 170 connects catheter 117, purge subsystem 150, and connector cable 160. In some implementations, plug 170 includes a memory for storing operating parameters. Repositioning unit 180 may be used to reposition blood pump 110.

As shown, purge subsystem 150 includes a container 151, a supply line 152, a purge cassette 153, a purge disc 154, purge tubing 155, a check valve 156, a pressure reservoir 157, an infusion filter 158, and a sidearm 159. Container 151 may, for example, be a bag or a bottle. A purge fluid is stored in container 151. Supply line 152 provides a fluidic connection between container 151 and purge cassette 153. Purge cassette 153 may control how the purge fluid in container 151 is delivered to blood pump 110. For example, purge cassette 153 may include one or more valves for controlling a pressure and/or flow rate of the purge fluid. Purge disc 154 includes one or more pressure and/or flow sensors for measuring a pressure and/or flow rate of the purge fluid. As shown, controller 130 interfaces with purge cassette 153 and purge disc 154. Purge tubing 155 provides a fluidic connection between purge disc 154 and check valve 156. Pressure reservoir 157 provides additional filling volume and pressure during a purge fluid change. In some implementations, pressure reservoir 157 includes a flexible rubber diaphragm that provides the additional filling volume and pressure by means of an expansion chamber. Infusion filter 158 helps prevent bacterial contamination and air from entering catheter 117. Sidearm 159 provides a fluidic connection between infusion filter 158 and plug 170.

During operation, controller 130 receives measurements from pressure sensor 114, the motor (not shown) within motor housing 116, and purge disc 154 and controls the motor (not shown) within motor housing 116 and purge cassette 153. As noted above, controller 130 controls and measures a pressure and/or flow rate of a purge fluid via purge cassette 153 and purge disc 154. During operation, after exiting purge subsystem 150 through sidearm 159, the purge fluid is channeled through a purge lumen (not shown) within catheter 117 and plug 170. Sensor cables (not shown) within catheter 117, connector cable 160, and plug 170 provide an electrical and/or optical connection between pressure sensor 114 and controller 130. Motor cables (not shown) within catheter 117, connector cable 160, and plug 170 provide an electrical connection between the motor within motor housing 116 and controller 130. During operation, controller 130 receives measurements from pressure sensor 114 through the sensor cables and controls the electrical power delivered to the motor within motor housing 116 through the motor cables. By controlling, for example, the current and/or voltage delivered to the motor within motor housing 116, controller 130 can control the speed of the motor within motor housing 116. In some implementations, controller 130 is connected to an external power source (e.g., a battery or an electrical outlet of a power grid). In some implementations, controller 130 comprises an internal power source (e.g., a battery). When electric power is supplied by means of a battery, a patient may be afforded a greater degree of mobility.

Various modifications can be made to ventricular support system 100 and one or more of its components. For example, ventricular support system 100 can be modified to accommodate a variety of different intravascular blood pumps, such as the Impella 2.5®, Impella 5.0®, Impella 5.5®, Impella LD®, Impella RP®, and Impella CP® catheters from Abiomed, Inc., Danvers, Mass. As another example, one or more sensors may be added to blood pump 100. For example, a second pressure sensor may be added to blood pump 100 near inlet area 112 that is configured to measure a left ventricular blood pressure. In such implementations, the second pressure sensor may operate in much the same way as pressure sensor 114. Furthermore, in such implementations, additional sensor cables may be disposed within catheter 117, connector cable 160, and plug 170 to provide an electrical connection between the one or more additional sensors and controller 130. As yet another example, one or more components of ventricular support system 100 may be separated. For example, display 140 may be incorporated into another device in communication with controller 130 (e.g., wirelessly or through one or more electrical cables). As yet another example, one or more of the sensor and/or motor cables described above can be replaced with a single electrical cable having a plurality of separate electrical conduits.

Figure 2:
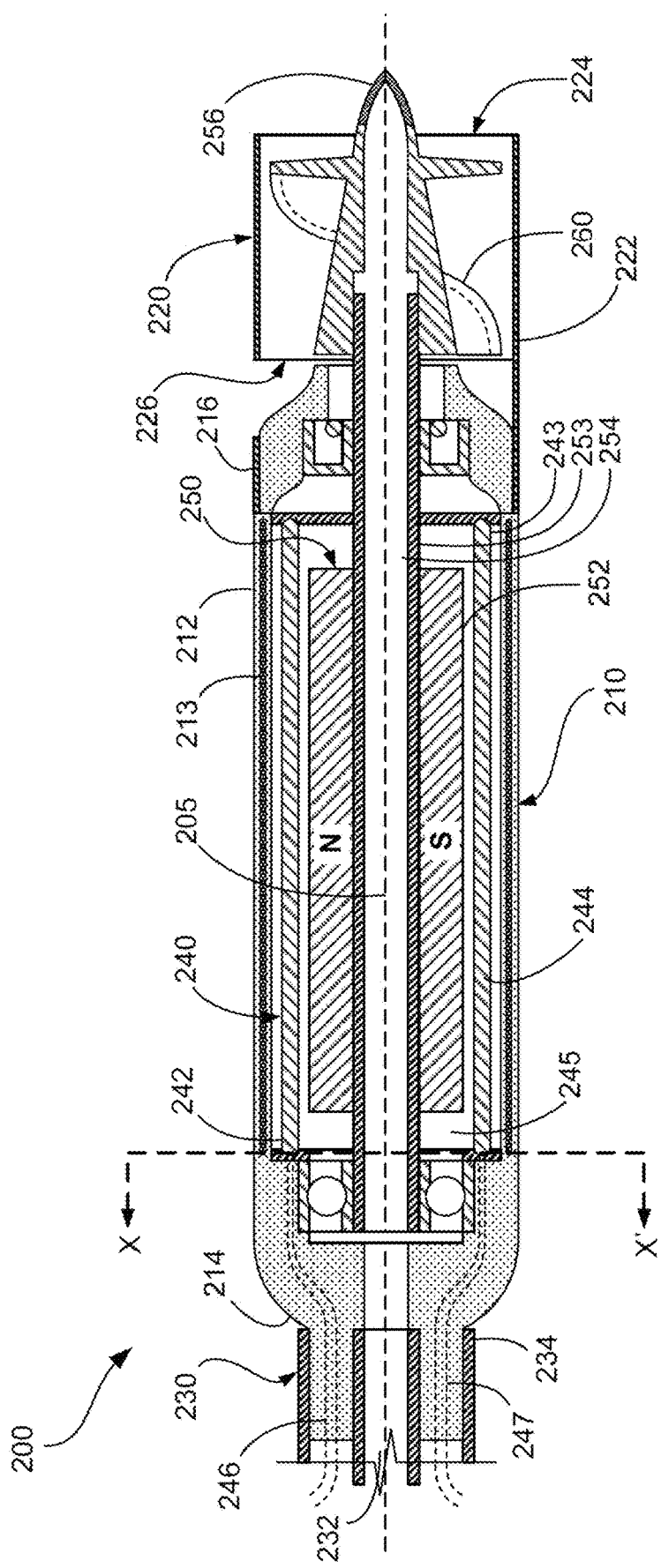
FIG. 2 illustrates aspects of the interior of an intravascular blood pump.

FIG. 2 illustrates aspects of the interior of an intravascular blood pump 200. In some implementations, blood pump 200 may be structured and operated in much the same way as blood pump 110. Furthermore, in some implementations, blood pump 200 may be incorporated into a ventricular support system, such as ventricular support system 100. As shown, blood pump 200 comprises a motor unit 210 and a pump unit 220 arranged along a longitudinal axis 205. Motor unit 210 comprises an electric motor including a stator 240 and a rotor 250 contained within a housing 212. Electric power is delivered to stator 240 through electrical conduits 246 and 247 extending through a catheter 230. In some implementations, the electric power may be provided by a controller (e.g., controller 130) connected to blood pump 200. In some implementations, a pressure sensor (e.g., pressure sensor 114) may be coupled to pump unit 200.

Housing 212 comprises a proximal end 214 and a distal end 216. Proximal end 214 of housing 212 is coupled to a distal end 234 of catheter 230, which may comprise a flexible tube. Catheter 230 comprises a lumen 232, which extends towards the physician (i.e., proximally) for control and operation of the blood pump 200. In FIG. 2, stator 240 and housing 212 are depicted as separate components. However, in other implementations, stator 240 may be encapsulated within housing 212 to form a single component.

Rotor 250 comprises a permanent magnet 252 that is rotationally supported about a shaft 253 within a central opening 245 of stator 240. Magnet 252 may comprise a cylindrical permanent magnet that surrounds shaft 253 within motor unit 210. Shaft 253 extends from motor unit 210 into pump unit 220 and facilitates rotation of an impeller 260 for the pumping of blood. In some implementations, shaft 253 may be rotationally supported by one or more contact-type bearings or bushings, such as the one illustrated in FIG. 7. In some implementations, shaft 253 may be rotationally supported by one or more non-contact-type bearings or bushings (e.g., a magnetic or hydrodynamic bearing). In some implementations, shaft 253 may be rotationally supported by a first bearing or busing positioned at proximal end 214 of housing 212 and a second bearing or bushing positioned at distal end 216 of housing 212. In some implementations, rotor 250 may comprise two or more permanent magnets attached to shaft 253, or an electromagnetic magnet having its own rotor windings. Further, while FIG. 2 illustrates rotor 250 as rotatable within stator 240, motor unit 210 may be configured such that stator 240 is held stationary about shaft 253 and rotor 250 is configured as a cylinder that rotates around stator 240.

Shaft 253 extends along the length of motor unit 210 and extends into a cylindrical housing 222 of pump unit 220. In some implementations, shaft 253 may be hollow and comprise a lumen 254 for the passage of a guidewire, for example. The distal end of shaft 253 is coupled to an impeller 260 located within housing 222. Interaction between stator 240 and rotor 250 of motor unit 210 generates torque in rotor 250 causing shaft 253 to rotate, which, in turn, causes impeller 260 to rotate in housing 222. When this occurs, blood may be drawn into blood pump 200 via an axial intake opening 224 for conveyance in the axial direction, the blood issuing laterally from openings 226 and flowing axially along housing 212. In this manner blood pump 200 generates a flow of blood within the heart of the patient. In some implementations, the blood flow may be reversed, such that during operation, blood may be drawn into openings 226, channeled through housing 222, and expelled through opening 224.

Stator 240 extends along the length of motor unit 210 from a proximal end 242 to a distal end 243, and comprises coils 244 wound in a particular pattern, the details of which will be provided below. In some implementations, stator 240 may comprise six coils. In other implementations, more or fewer coils may be provided (e.g., two coils, three coils, four coils, five coils, or more than six coils). Preferably, the number of coils is even so that diametrically opposed coils may form pairs (e.g., with respect to control of a magnetic field) and be controlled simultaneously. As shown in FIG. 2, stator 240 defines opening 245 in which rotor 250 is positioned. In some implementations, stator 240 is slotless, such that the coils 244 are wound upon themselves and not onto a laminated stator core. Each of the coils 244 may have an insulating coating (not shown), and, optionally, the stator 240 may be enmolded by a synthetic epoxide resin (also not shown).

As shown, motor unit 210 also comprises a yoke 213 that is contained within housing 212. Yoke 213 carries the magnetic flux produced by the permanent magnet poles of rotor 250. Yoke 213 may be made of a magnetic material, such as steel, or a suitable alloy, such as cobalt steel. Yoke 250 may enhance the magnetic flux, which allows for reduction of the overall diameter of the blood pump 200. In other implementations, housing 212 may serve as yoke 213. Since yoke 213 is the outermost component of motor unit 210, its diameter and/or thickness limits the size of stator 240.

FIGS. 3(a)-(d) illustrate the individual winding turn structures of coil winding patterns 310-313. However, it will be understood that a complete stator, such as stator 240 in FIG. 2, may be obtained by the axial and angular arrangement of a plurality of wire turns about a longitudinal axis of a motor unit, such as longitudinal axis 205. FIGS. 3(e)-(h) illustrate the coil winding patterns for a complete stator for each of the coil winding types in FIGS. 3(a)-(d), respectively. The horizontal axis of each of the plots in FIGS. 3(e)-(h) represents the angular position along the circumference of the respective stator and the vertical axis represents the longitudinal length of the respective stator moving from the distal end to the proximal end of the stator.

FIG. 3(a) illustrates an individual coil winding pattern 310 in which each wire 314 in the coil extends from a proximal end 321, along the length of the coil, to a distal end 325. At distal end 325, wire 314 follows the external perimeter of stator for 180 degrees and returns to proximal end 321. A complete coil winding pattern formed by coils having the turns illustrated in FIG. 3(a) is shown in FIG. 3(e).

FIG. 3(b) illustrates an individual rhombic coil winding pattern 311 in which each wire 315 is arranged in a bent configuration. Unlike coil winding pattern 310 of FIG. 3(a), coil winding pattern 311 comprises one continuous wire that is wound several times over, each complete turn shifted angularly. The bent configuration of the rhombic coil winding pattern when adopted in a stator may require post-assembly of the coils of each individual phase. A complete coil winding pattern having the rhombic coil winding pattern illustrated in FIG. 3(b) is shown in FIG. 3(f).

FIG. 3(c) illustrates an individual helical coil winding pattern 312 in which each wire 316 is arranged in an elliptical configuration. Coil winding pattern 312 is similar to coil winding pattern 311 of FIG. 3(b), but without the bend, which simplifies the coil winding process. The helical coil winding is a one-step winding which can be easily formed without the need for any post-assembly steps. A complete coil winding pattern having the helical coil winding pattern illustrated in FIG. 3(c) is shown in FIG. 3(g).

FIG. 3(d) illustrates an individual hybrid coil winding pattern 313 that comprises a coil winding that is a mixture of coil winding pattern 310 of FIG. 3(a) and coil winding pattern 311 of FIG. 3(b). Such a hybrid coil winding allows for an optimum ratio of torque to resistance by adjusting the horizontal to vertical aspect ratio of the coil. A complete coil winding comprising the hybrid coil winding patterns illustrated in FIG. 3(d) is shown in FIG. 3(h).

Figure 4:
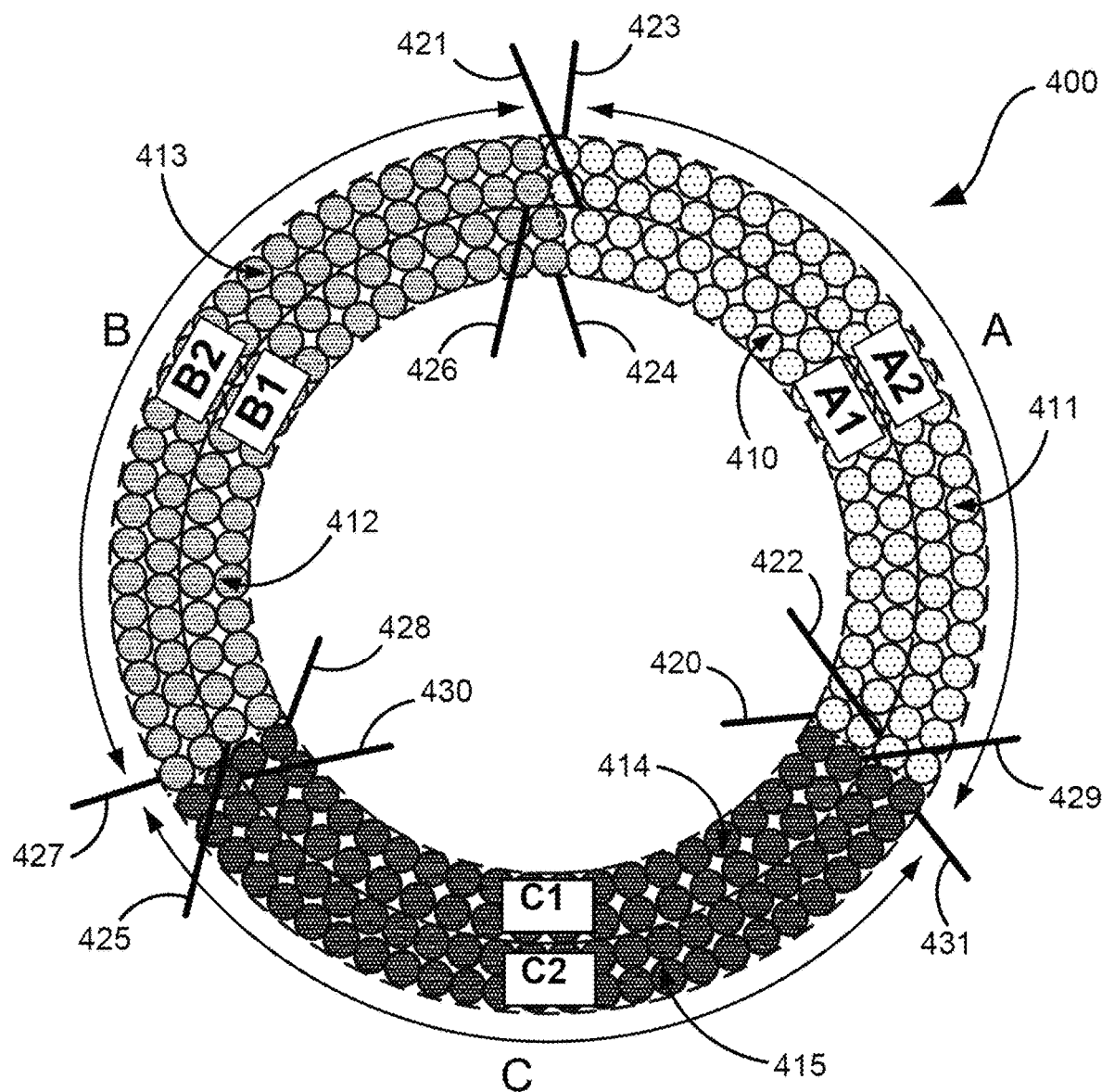
FIG. 4 illustrates a cross-sectional view of a stator.

FIG. 4 illustrates a stator 400 comprising two coils per phase per magnet pole pair for use in a three-phase two-pole electric motor. Stator 400 may be a double-winding stator (or a four-layer coil stator). Stator 400 may employ any of coil winding patterns 310-313. When implemented with, for example, coil winding pattern 312 of FIG. 3(c), stator 400 is a double helical winding stator similar to the complete winding illustrated in FIG. 3(g). In stator 400, each phase A, B, and C of the three-phase electric motor comprises two coils. Thus, phase A comprises coil 410 (labelled "A1") and coil 411 (labelled "A2"), phase B comprises coil 412 (labelled "B1") and coil 413 (labelled "B2"), and phase C comprises coil 414 (labelled "C1") and coil 415 (labelled "C2"). As shown, stator 400 has an inner winding comprising coils A1, B1 and C1, and an outer winding comprising coils A2, B2 and C2. In some implementations, each of coils A2, B2 and C2 in the outer winding has a greater number of turns than each of coils A1, B1 and C1 in the inner winding. As shown, each of coils 410-415 has a start point and an end point, as indicated by lead wires 420-431. In some implementations, lead wires 420-431 are located at the proximal end of stator 400 for connectivity with the feed lines (e.g., electrical conduits 246 and 247). In some implementations, coils 410-415 may be formed from insulated magnet wires.

In some implementations, coil A1 is formed by winding the coil from a first end 420 along the circumference of stator 400 about a 120 degree span of the coil in a first direction (e.g., anticlockwise) until the end of the span of the coil where it forms a second end 421. After forming coil A1, the coils comprising the rest of the inner winding (i.e., coils B1 and C1) may then be formed. After coils A1, B1 and C1 are formed, coils A2, B2 and C2 may be formed. Coil A2 may be formed by winding the coil from a first end 422 along the circumference of stator 400 about a 120 degree span of the coil in a first direction (e.g., anticlockwise) until the end of the span of the coil where it forms a second end 423. After forming coil A2, the coils comprising the rest of the outer winding (i.e., coils B2 and C2) may then be formed. This winding sequence may help reduce the overall size of stator 400. As shown, coils 410-415 are distributed equally along the circumference of stator 400 within the inner or outer winding. However, in other implementations, coils 410-415 may be distributed unequally.

Figure 5:
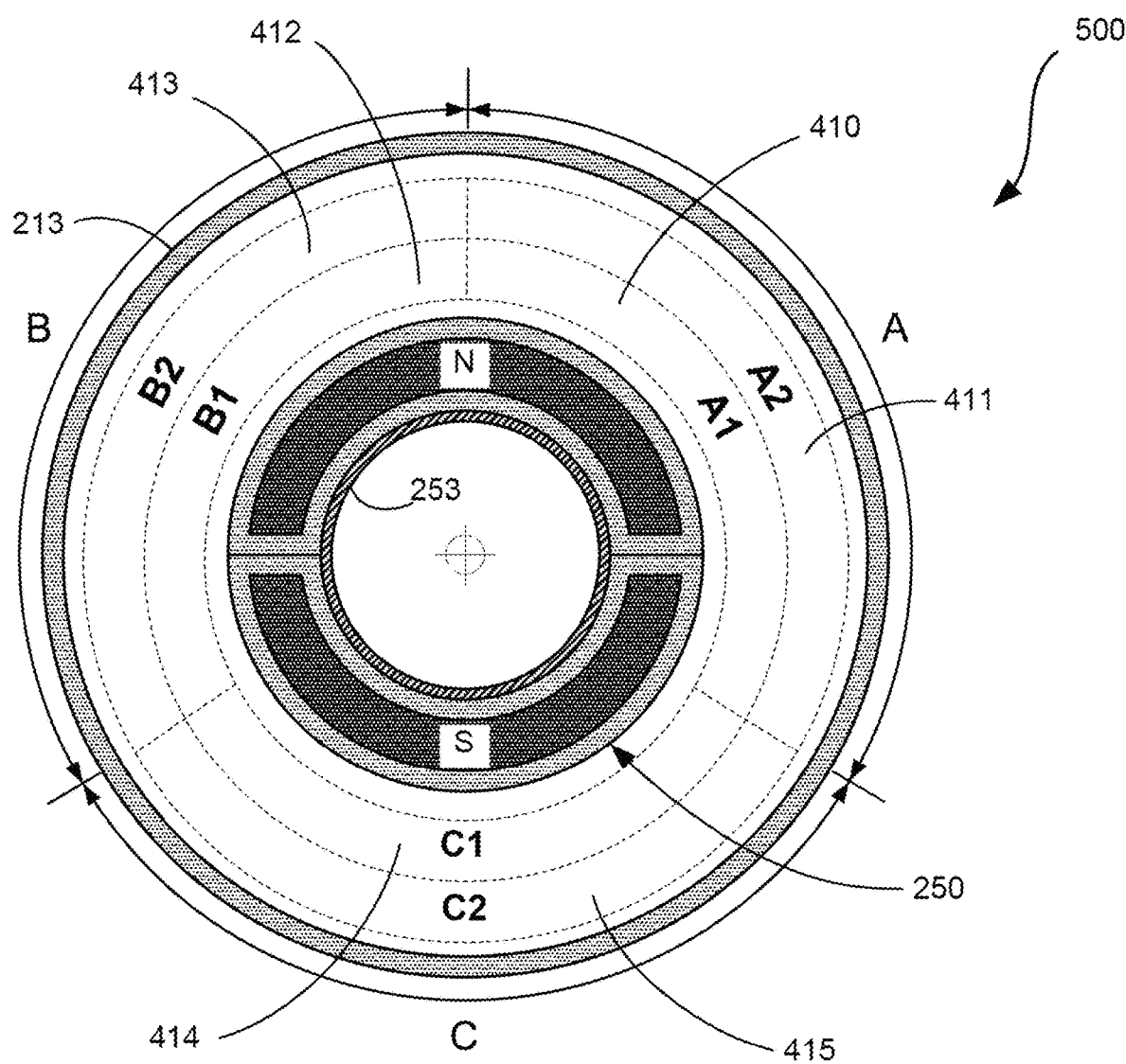
FIG. 5 illustrates a cross-sectional view of the stator of FIG. 4 as used in the blood pump of FIG. 2.
Figure 6A:
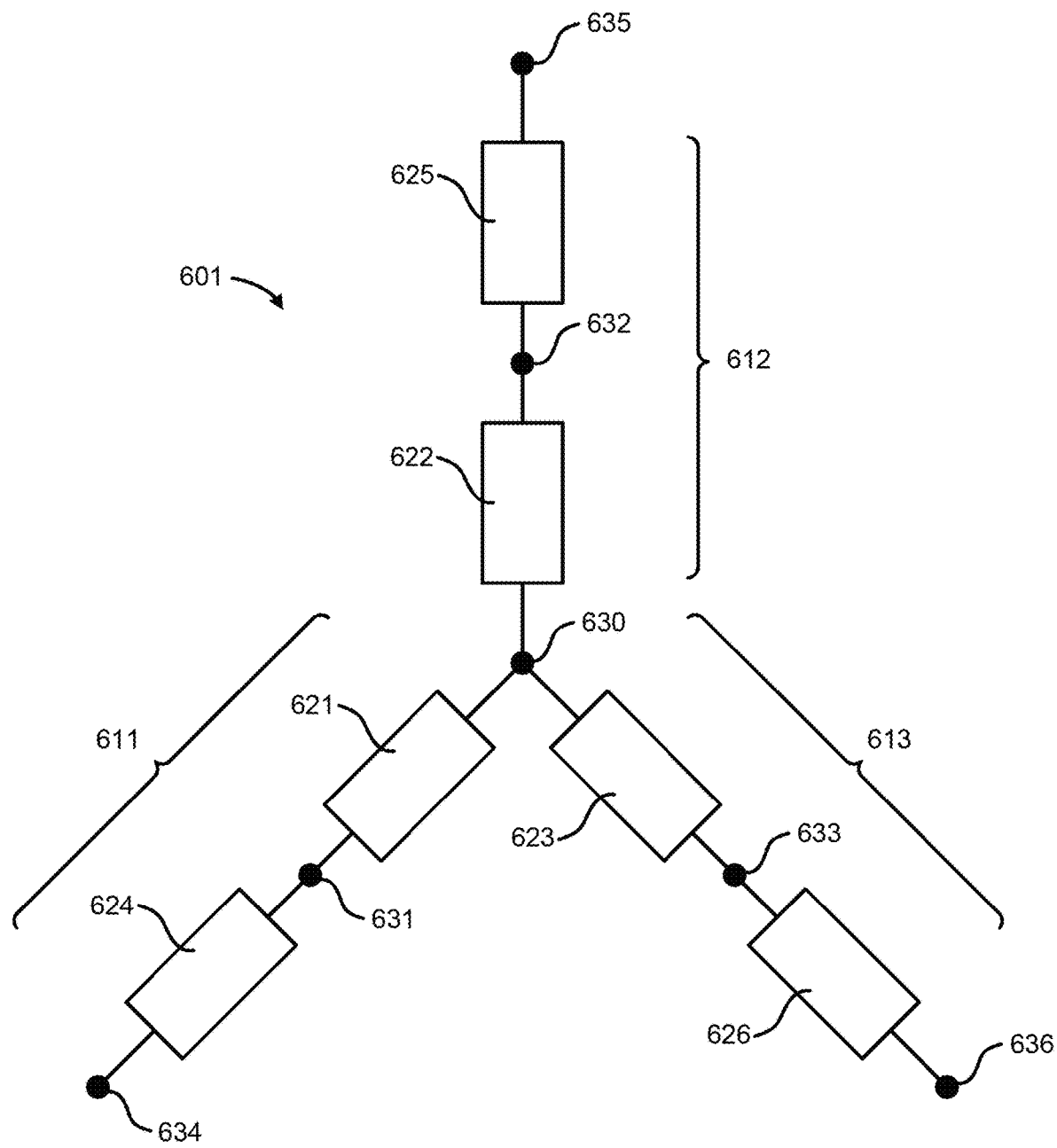
FIG. 6(a) illustrates a star or wye circuit configuration.
Figure 6B:
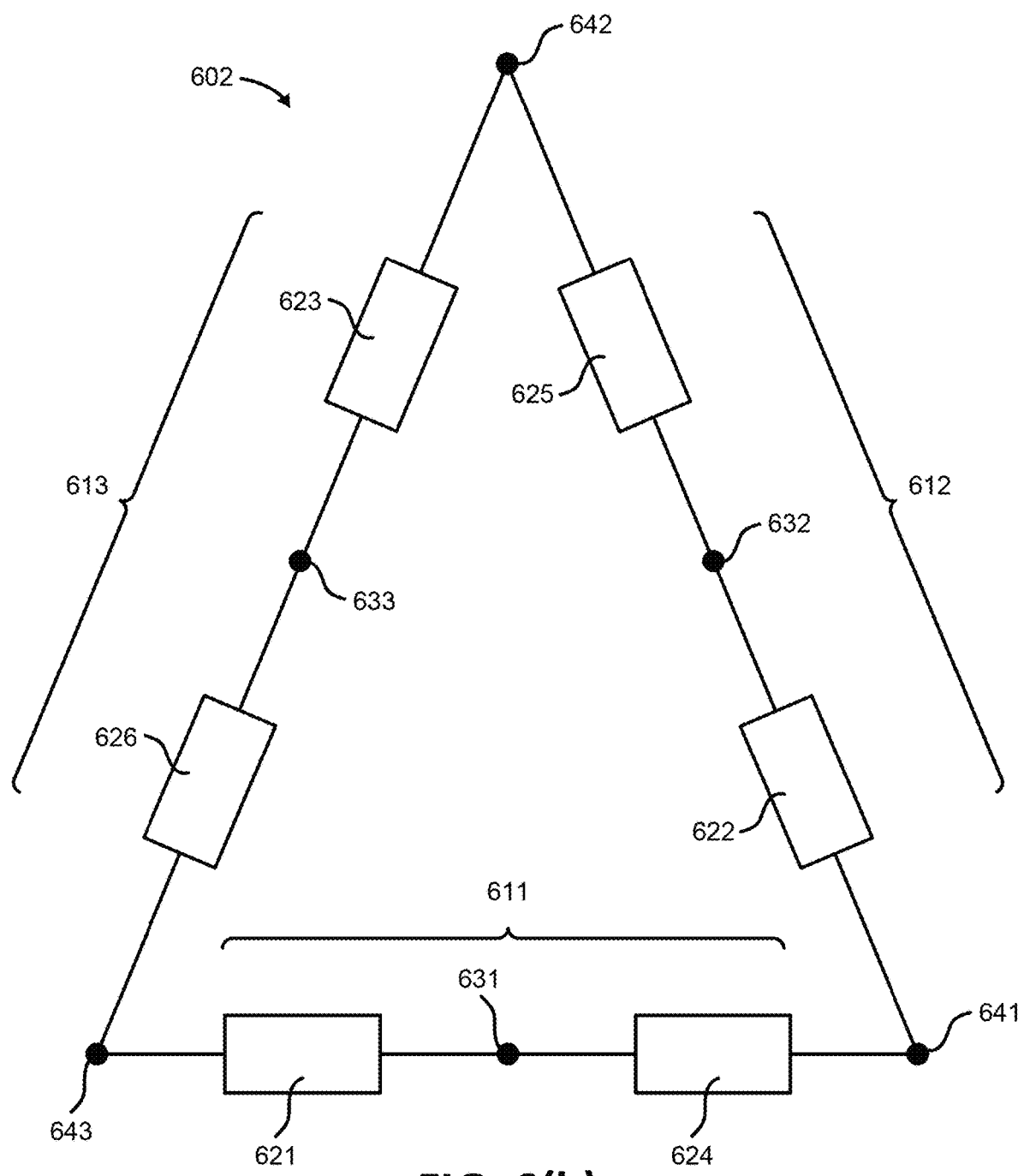
FIG. 6(b) illustrates a delta circuit configuration.
Figure 6C:
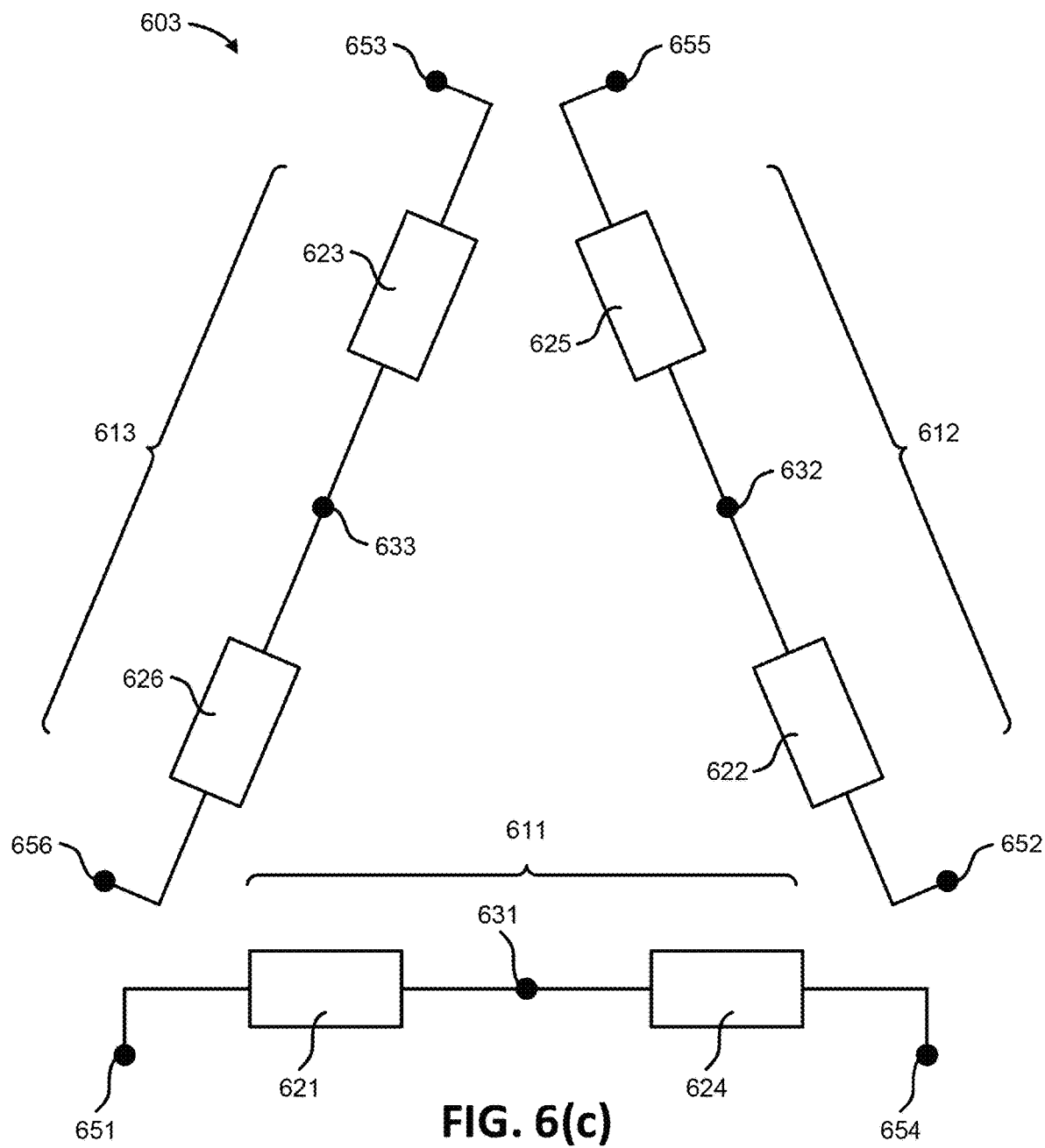
FIG. 6(c) illustrates an "open end windings" circuit configuration.
Figure 6D:
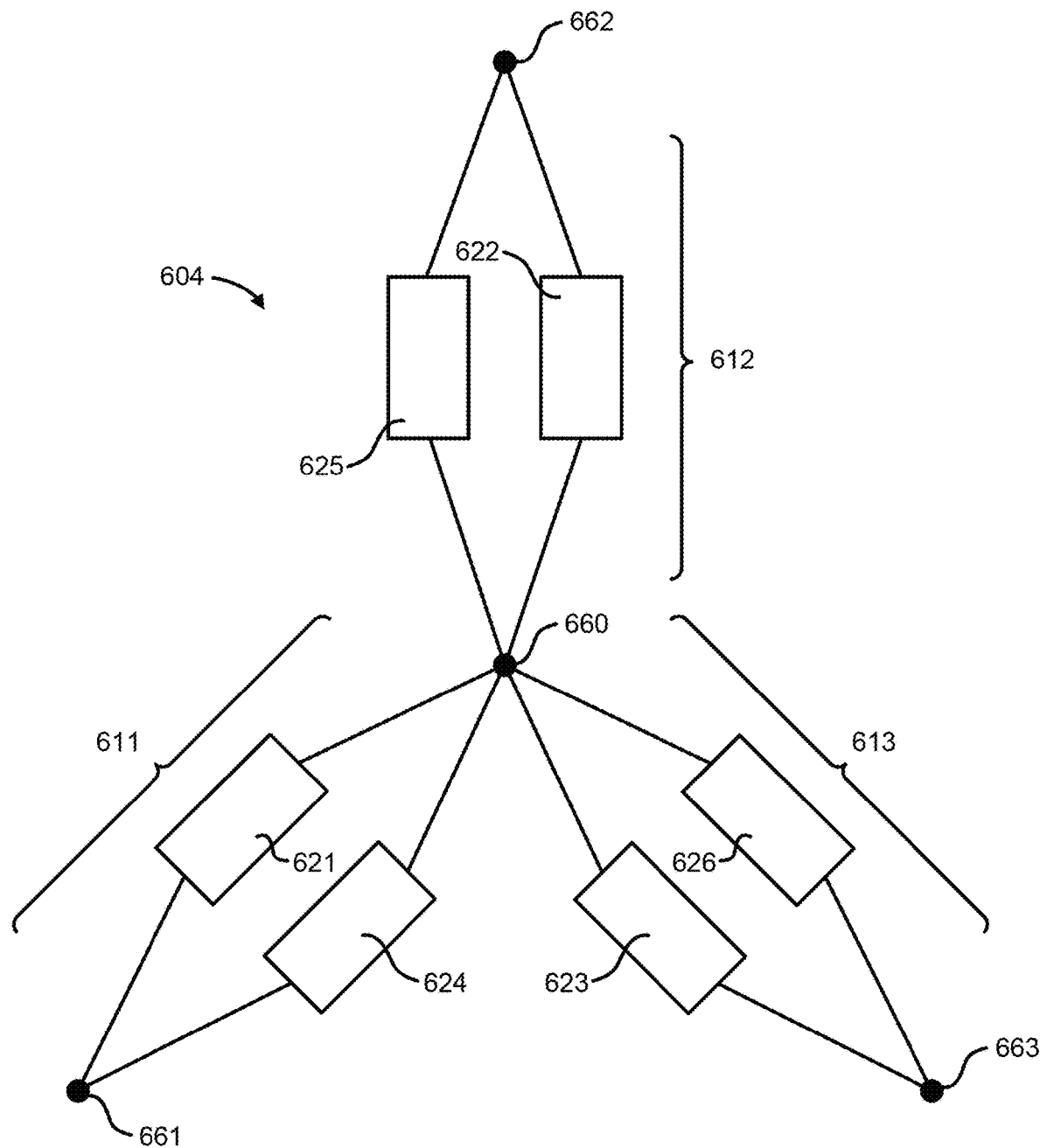
FIG. 6(d) illustrates a star or wye circuit configuration.

FIG. 5 illustrates a cross-section 500 of blood pump 200 about line X-X' of FIG. 2 employing stator 400 of FIG. 4 in a three-phase two-pole electric motor. For clarity, the windings forming coils 410-415 are omitted from FIG. 5. As described in relation to FIG. 2, rotor 250 is in constant rotation when in use. FIG. 5 depicts the position of rotor 250 at a particular instance in time. In the illustrated position, rotor 250 produces a magnetic flux density B, and each of coils 410-415 carry a current that may be directed longitudinally (into the page or out of the page). According to Lorentz force law, the interaction between the magnetic flux density B and the longitudinal length of the current-carrying wire L in a direction perpendicular to the magnetic flux density B generates a torque T within rotor 250 for rotation thereof, governed by the equation:

$$T \propto (L\hat{z} \times B\hat{r}), \quad (1)$$

where $\hat{z}$ is a direction parallel to the longitudinal axis 205 of rotor 250, $\hat{r}$ is a radial direction of the magnetic flux density B that is perpendicular to longitudinal axis 205 of rotor 250, and x denotes the vector cross product. Thus, the flow of current in stator 400 causes rotation of rotor 250 about longitudinal axis 205, which, in turn, causes a corresponding rotation of impeller 260 coupled to the distal end of shaft 253.

Additional information regarding the structure and operation of the intravascular blood pumps described above in relation to FIGS. 2-5 can be found in U.S. application Ser. No. 16/909,028, which was filed on Jun. 23, 2020, and is incorporated herein by reference. In other implementations, the interior of an intravascular blood pump may be structured differently. For example, in some implementations, coils 244 may be wound upon a laminated stator core as described in E.P. Application No. 17191940.0, which was filed on Sep. 19, 2017 and published as E.P. Publication No. 3456367 A1, and E.P. Application No. 17155078.3, which was filed on Feb. 7, 2017 and published as E.P. Publication No. 3357523 A1, both of which are incorporated herein by reference.

FIGS. 6(*a*)-(*d*) illustrate circuitry configurations for a stator (e.g., stators 240 or 400) of an intravascular blood pump (e.g., blood pumps 110 or 200). As shown, circuit configurations 601-604 include branches 611-613. Branch 611 includes coils 621 and 624, which may be wound upon themselves (see, e.g., coils 410-415). Branch 612 includes coils 622 and 625, which may be wound upon themselves (see, e.g., coils 410-415). Branch 613 includes coils 623 and 626, which may be wound upon themselves (see, e.g., coils 410-415). In some implementations, each of coils 621-626 may have a single electrical conduit (e.g., an insulated magnet wire). In other implementations, one or more of coils 621-626 may include two or more electrical conduits connected in parallel. In some implementations, one or more of circuit configurations 601-604 may include more or fewer coils (e.g., two coils, three coils, four coils, five coils, or more than six coils).

As shown in FIG. 6(*a*), circuit configuration 601 is a star or wye circuit configuration. In circuit configuration 601, coils 621-623 are electrically connected at node 630. Coils 621 and 624 are electrically connected at node 631. Coils 622 and 625 are electrically connected at node 632. Coils 623 and 626 are electrically connected at node 633. Coils 624, 625, 626 may be electrically connected to separate electrical conduits of a motor cable (e.g., electrical conduits 246 and 247) at nodes 634, 635, and 636, respectively. During operation, three-phase electrical power may be provided by a controller (e.g., controller 130) to a stator of an intravascular blood pump. For example, three separate signals having a 120 degree phase difference may be delivered to coils 624, 625, and 626 through three separate electrical conduits of a motor cable and nodes 634, 635, and 636, respectively. In some implementations, these signals may be oscillating signals (e.g., alternating current (AC) signals).

As shown in FIG. 6(*b*), circuit configuration 602 is a delta circuit configuration. Circuit configuration 602 includes many of the same components as circuit configuration 601. However, circuit configuration 602 does not include node 630. Instead, circuit configuration 602 includes nodes 641-643. Coils 622 and 624 are electrically connected at node 641. Coils 623 and 625 are electrically connected at node 642. Coils 621 and 626 are electrically connected at node 643. During operation, a controller (e.g., controller 130) may provide three-phase electrical power to coils 621-626 through three separate electrical conduits of a motor cable (e.g., electrical conduits 246 and 247) and nodes 641-643. For example, a first signal may be delivered through a first conduit (not shown) of a motor cable and node 641 to coils 622 and 624, a second signal may be delivered through a second conduit (not shown) of the motor cable and node 642 to coils 623 and 625, and a third signal may be delivered through a third conduit (not shown) of the motor cable and node 643 to coils 621 and 626. In some implementations, the first, second, and third signals may have a 120 degree phase difference. In some implementations, the first, second, and third signals may be oscillating signals (e.g., alternating current (AC) signals).

As shown in FIG. 6(*c*), circuit configuration 603 is a configuration with open wiring ends, commonly called an "open end windings" circuit configuration. Circuit configuration 603 includes many of the same components as circuit configuration 601. However, circuit configuration 603 does not include node 630. Instead, circuit configuration 603 includes nodes 651-656. During operation, a controller (e.g., controller 130) may separately provide electrical power to each of branches 611-613 through three separate pairs of electrical conduits of a motor cable (e.g., electrical conduits 246 and 247) and nodes 651-656. For example, in some implementations, a controller may provide three-phase electrical power to each of branches 611-613 through three separate pairs of electrical conduits of a motor cable and nodes 651-656. In some implementations, three separate signals having a 120 degree phase difference may be delivered to branches 611-613. In some implementations, these signals may be oscillating signals (e.g., alternating current (AC) signals).

In circuit configurations 601-603, coils 621-626 are arranged as pairs of coils in series. For example, within branch 611, coils 621 and 624 are arranged in series. However, in other implementations, coils 621-626 may be arranged as pairs of coils in parallel. For example, as shown in FIG. 6(*d*), circuit configuration 601 may be rearranged to form circuit configuration 604, which is also a star or wye circuit configuration.

As noted above, more or fewer coils may be included in circuit configurations 601-604. When the number of coils is increased or decreased, the number of signals delivered to branches 611-613 may also be increased or decreased. For example, in implementations where branch 613 is removed from circuit configurations 601-604, a controller may provide two-phase electrical power to branches 611 and 612. In some such implementations, two separate signals having a 90 or 180 degree phase difference may be delivered to branches 611 and 612. As another example, in implementations where branches 612 and 613 are removed from circuit configurations 601-604, a controller may provide single-phase electrical power to branch 611. As yet another example, in implementations where a fourth branch is added to circuit configurations 601-604, a controller may provide four-phase electrical power to branches 611-613 and the fourth branch. In some such implementations, four separate signals having a 90 degree phase difference may be delivered to branches 611-613 and the fourth branch.

Figure 7:
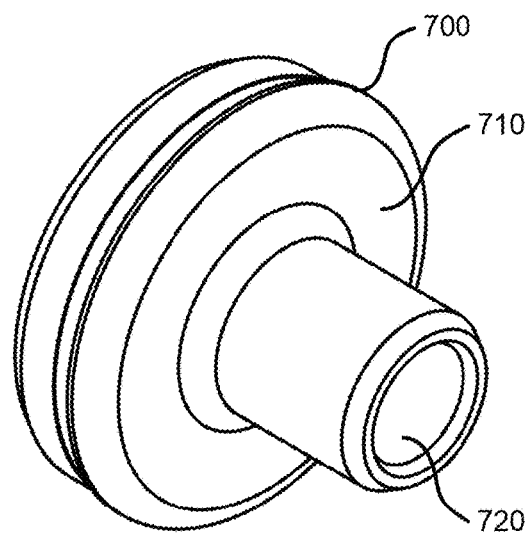
FIG. 7 illustrates a bearing.

FIG. 7 illustrates a bearing 700. As shown, bearing 700 includes a top surface 710 and a central opening 720. In some implementations, bearing 700 may be positioned within a proximal end of a housing of a motor unit (e.g., proximal end 214 of housing 212) of an intravascular blood pump (e.g., blood pump 200). In some implementations, bearing 700 may be used as the yoke of a blood pump. In such implementations, bearing 700 may be made of a magnetic material, such as steel, or a suitable alloy, such as cobalt steel. In other implementations, bearing 700 may be shaped differently.

Figure 8A:
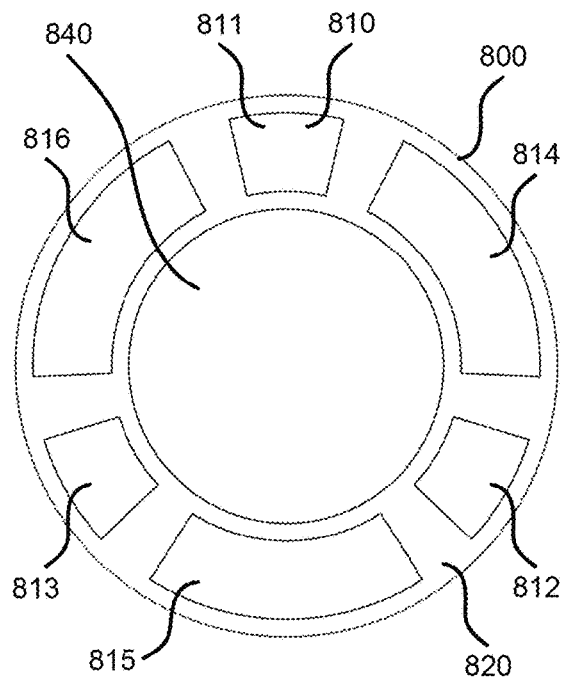
FIGS. 8(a) and 8(b) illustrate a printed circuit board (PCB).
Figure 8B:
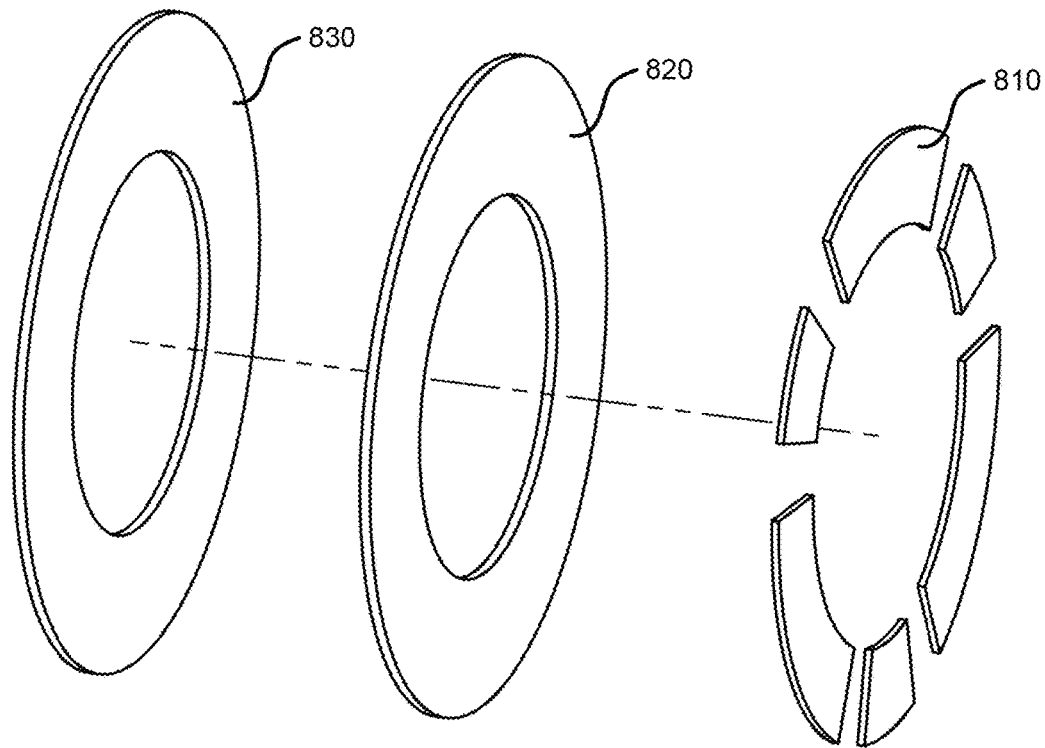

FIGS. 8(a) and 8(b) illustrate a printed circuit board (PCB) 800. FIG. 8(a) illustrates a top-down view of PCB 800. FIG. 8(b) illustrates an exploded view of PCB 800. As shown PCB 800 includes layers 810, 820, and 830 and a central opening 840. Layer 810 includes pads 811-816. Layer 810 may be made of an electrically conductive material (e.g., copper or silver). Layer 820 may be made of an electrically insulating material (e.g., polyimide). Layer 830 may be made of an adhesive material. Pads 811-816 of PCB 800 may be used to form the circuit configurations described above in relation to FIGS. 6(a)-(d). Furthermore, PCB 800 may be coupled to top surface 710 of bearing 700 through the adhesive material of layer 830. In such implementations, central opening 840 may correspond in shape to central opening 720 of bearing 700, and its wall thickness. However, central opening 840 may be wider than central opening 720.

As noted above, pads 811-816 may be used to form the nodes of the circuit configurations described above in relation to FIGS. 6(a)-(d). For example, in relation to circuit configuration 601, pads 811-813 may be used to form nodes 631-633 and pads 814-816 may be used to form nodes 634-636. In such implementations, node 630 may be formed without the use of PCB 800 (e.g., by twisting and soldering the appropriate wires together). As another example, in relation to circuit configuration 602, pads 811-813 may be used to form nodes 631-633 and pads 814-816 may be used to form nodes 641-643. In such implementations the coils (e.g., coils 244 or 410-415) of an intravascular blood pump (e.g., blood pumps 110 or 200) may be coupled to each other or electrical conduits of a motor cable (e.g., electrical conduits 246 and 247). As shown, pads 814-816 are larger than pads 811-813. In relation to circuit configurations 601 and 602, this may be advantageous because manually soldering the coils to the electrical conduits of the motor cable may be more difficult than manually soldering the coils to each other.

Various modifications can be made to PCB 800. For example, PCB 800 may include more or fewer pads (e.g., two pads, three pads, four pads, five pads, or more than six pads) and/or layers (e.g., one layer, two layers, four layers, or more than five layers). For example, in order to implement circuit configuration 601, an additional pad may be added to PCB 800 (e.g., for node 630). As another example, in order to implement circuit configuration 603, three additional pads may be added to PCB 800. As yet another example, in order to implement circuit configuration 604, two of pads 811-816 may be removed and one or more of the remaining pads may be enlarged. In other implementations, pads 811-816 may be shaped differently. For example, each of pads 811-816 may have the same size and/or shape. Similarly, in other implementations, PCB 800 may be shaped differently. For example, in implementations where a shaft (e.g., shaft 253) does not extend through a bearing (e.g., bearing 700) of an intravascular blood pump (e.g., blood pumps 110 or 200), central opening 840 may be removed from PCB 800. In such implementations, central opening 840 may be replaced with one or more additional electrical connections (e.g., one or more additional pads). Furthermore, in such implementations, the size and/or position of pads 811-816 may be adjusted. For example, the size of pads 811-816 may be increased to further reduce the risk of unintentionally shorting coils (e.g., coils 244 or 410-415) and/or electrical conduits of a motor cable (e.g., electrical conduits 246 and 247).

Figure 9A:
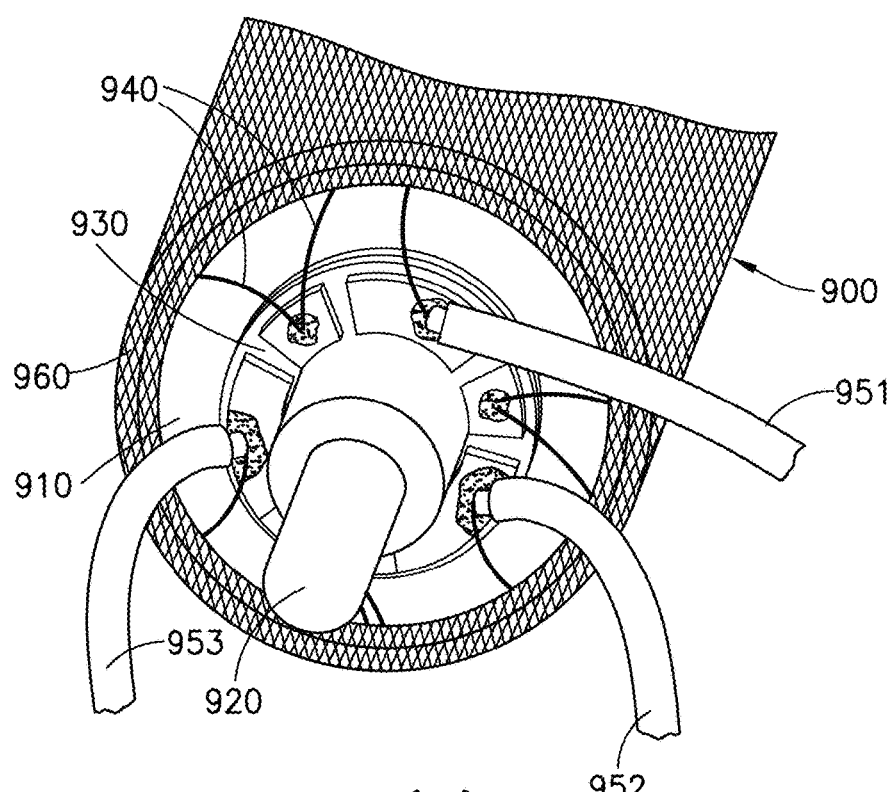
FIGS. 9(a) and 9(b) are illustrations of an intravascular blood pump.
Figure 9B:
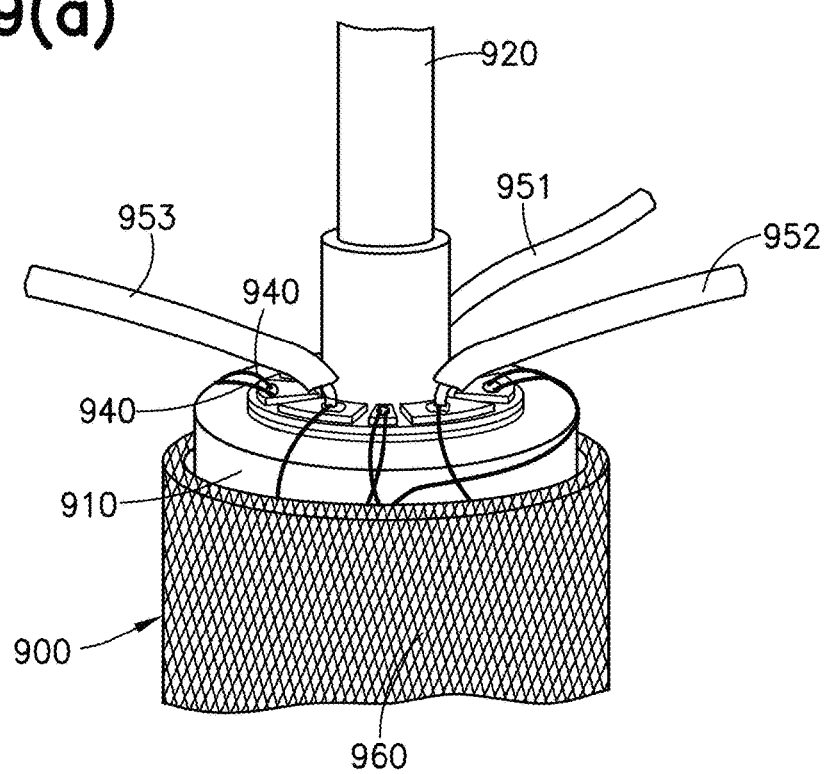

FIGS. 9(a) and 9(b) illustrate aspects of the interior of an intravascular blood pump 900. Blood pump 900 may be structured and operated in much the same way as blood pumps 110 and 200. Furthermore, blood pump 900 may be incorporated into a ventricular support system, such as ventricular support system 100. As shown, blood pump 900 includes bearing 910, shaft 920, PCB 930, coils 940, electrical conduits 951-953, and stator 960. Bearing 910 may be structured in much the same way as bearing 700. Shaft 920 may be a temporary assembly fixture that is removed during assembly. PCB 930 may be structured in much the same way as PCB 800. Coils 940 may be structured in much the same way as 410-415. Electrical conduits 951-953 may be included in a motor cable. Stator 960 may be structured in much the same way as stator 400. As shown in FIG. 9(b), during assembly, coils 940 and electrical conduits 951-953 may be manually soldered to PCB 930. Due to the small size of blood pump 900, the soldering process can be difficult and there is a risk of unintentionally shorting coils 940 and/or electrical conduits 951-953.

FIGS. 10(a)-(c) illustrate aspects of a motor cable 1000 that can be used to reduce the risk of shorting coils (e.g., coils 244 410-415, or 940) and/or electrical conduits (e.g., electrical conduits 246, 247, or 951-953) of a motor cable during the assembly of an intravascular blood pump (e.g., blood pumps 110, 200, or 900). As shown, cable 1000 includes a top layer 1001 of FIG. 10(a), a middle layer 1002 of FIG. 10(b), a bottom layer 1003 of FIG. 10(c), electrical conduits 1011-1013, input pads 1021-1023, output pads 1031-1033, connection pads 1041-1044, through holes 1051-1056 and 1061-1064, a tail portion 1070, a head portion 1080, and a central opening 1081. Layers 1001-1003 may be made of an electrically conductive material (e.g., copper or silver) and separated by one or more layers (not shown) an electrically insulating material (e.g., polyimide and/or adhesive). When assembled, top layer 1001 rests above middle layer 1002, which in turn, rests above bottom layer 1003. In some implementations, cable 1000 may include a coating (e.g., polyimide and/or adhesive) above top layer 1001 and/or below bottom layer 1003. Through holes 1051-1056 and 1061-1064 may be lined and/or filled with an electrically conductive material (e.g., copper or silver) to provide electrical connections between layers 1001-1003. In some implementations, motor cable 1000 may a flexible ribbon cable and/or a continuous printed circuit.

As shown, electrical conduit 1011 includes portions of layers 1001-1003, input pad 1021, output pad 1031, and through holes 1051-1053, 1061, and 1062. During operation, a controller (e.g., controller 130) may provide a first signal to one or more coils (e.g., coils 244, 410-415, or 940) of an intravascular blood pump (e.g., blood pumps 110, 200, or 900) through electrical conduit 1011. Electrical conduit 1012 includes portions of layers 1001-1003, input pad 1022, output pad 1032, and through holes 1054-1056, 1063, and 1064. During operation, a controller may provide a second signal to one or more coils of an intravascular blood pump through electrical conduit 1012. Electrical conduit 1013 includes portions of layer 1001, input pad 1023, and output pad 1033. During operation, a controller may provide a third signal to one or more coils of an intravascular blood pump through electrical conduit 1013.

During assembly, input pads 1021-1023 may be coupled to a connector or soldered to an electrical conduit (e.g., a portion of plug 170) for interfacing with a controller (e.g., controller 130). Furthermore, during assembly, output pads 1031-1033 and connection pads 1041-1044 may be used to form the circuit configurations described above in relation to FIGS. 6(*a*)-(*d*). For example, in relation to circuit configuration 601, connection pads 1041-1044 may be used to form nodes 630-633 and output pads 1031-1033 may be used to form nodes 634-636. As another example, in relation to circuit configuration 602, connection pads 1041-1044 may be used to form nodes 631-633 and output pads 1031-1033 may be used to form nodes 641-643. In some such implementations, one of connection pads 1041-1044 may be unused. Alternatively, in other implementations, one of connection pads 1041-1044 may be removed from cable 1000. During assembly, cable 1000 may be bent at or near the interface between tail portion 1070 and head portion 1080 at an angle between, for example, 45 and 135 degrees.

In relation to, for example, blood pump 900 of FIGS. 9(*a*) and 9(*b*), cable 1000 may replace PCB 930 and electrical conduits 951-953. For example, head portion 1080 may be viewed as replacing PCB 930 and tail portion 1070 may be viewed as replacing electrical conduits 951-953. In such implementations, head portion 1080 may be connected to bearing 910 through the use of an adhesive. For example, an adhesive layer (not shown) may be included in head portion 1080 beneath bottom layer 1003. Advantageously, this substitution reduces the amount of manual soldering required to assemble blood pump 900. For example, there is no longer a need to solder electrical conduits 951-953 to PCB 930 since tail portion 1070 and head portion 1080 are already connected to one another. Furthermore, as noted above, manually soldering coils 940 to electrical conduits 951-953 may be more difficult than manually soldering coils 940 to each other. As a result, there is an overall reduced complexity, and reduced risk of unintentionally shorting coils and/or electrical conduits. For example, eliminating the solder connection of electrical conduits 951-953 to PCB 930 reduces the risk of electrically shorting the solder joints or the electrical conduits themselves to the motor housing.

Various modifications can be made to cable 1000. For example, cable 1000 may include more or fewer pads. For example, as noted above, in order to implement circuit configuration 602, one of connection pads 1041-1044 may be removed from cable 1000. As another example, in order to implement circuit configuration 603, two additional connection pads may be added to cable 1000. As yet another example, in order to implement circuit configuration 604, three of connection pads 1041-1044 may be removed. In other implementations, cable 1000 may include more or fewer through holes. For example, additional through holes may be added to further improve or reconfigure the electrical connection between layers 1001-1003. Due to the overall size constraints of an intravascular blood pump, this may be more effective than increasing the size of through holes 1051-1056 and/or 1061-1064. For example, increasing the size of through holes 1051-1056 and/or 1061-1064 may require widening tail portion 1070. In other implementations, input pads 1021-1023, output pads 1031-1033, and/or connection pads 1041-1044 may be shaped differently. For example, each of input pads 1021-1023, output pads 1031-1033, and/or connection pads 1041-1044 may have the same size and/or shape. Similarly, in other implementations, cable 1000 may be shaped differently. For example, in implementations where a shaft (e.g., shafts 253 or 920) does not extend through a bearing (e.g., bearing 700 or 910) of an intravascular blood pump (e.g., blood pumps 110, 200, or 900), central opening 1081 may be removed from cable 1000. In such implementations, central opening 1181 may be replaced with one or more additional electrical connections (e.g., one or more additional pads). Furthermore, in such implementations, the size and/or position of output pads 1031-1033 and/or connection pads 1041-1044 may be adjusted. For example, the size of output pads 1031-1033 and/or connection pads 1041-1044 may be increased to further reduce the risk of unintentionally shorting coils (e.g., coils 244, 410-415, or 940) and/or electrical conduits 1011-1013. In other implementations, there may be more or fewer layers in cable 1000. For example, cable 1000 may include one or two conductive layers, with applicable pad and through-hole configurations, or cable 1000 may include four, five or more conductive layers, with applicable pad and through-hole configurations.

FIGS. 11(*a*)-(*c*) illustrate aspects of a motor cable 1100 that can be used to reduce the risk of shorting coils (e.g., coils 244, 410-415, or 940) and/or electrical conduits (e.g., electrical conduits 246, 247, or 951-953) of a motor cable during the assembly of an intravascular blood pump (e.g., blood pumps 110, 200, or 900). As shown, cable 1100 includes a top layer 1101 of FIG. 11(*a*), a middle layer 1102 of FIG. 11(*b*), a bottom layer 1103 of FIG. 11(*c*), electrical conduits 1111-1113, input pads 1121-1123, output pads 1131-1133, connection pads 1141-1144, through holes 1151-1156 and 1161-1163, a tail portion 1170, a head portion 1180, and a central opening 1181. Layers 1101-1103 may be made of an electrically conductive material (e.g., copper or silver) and separated by one or more layers (not shown) an electrically insulating material (e.g., polyimide and/or adhesive). When assembled, top layer 1101 rests above middle layer 1102, which in turn, rests above bottom layer 1103. In some implementations, cable 1100 may include a coating (e.g., polyimide and/or adhesive) above top layer 1101 and/or below bottom layer 1103. Through holes 1151-1156 and 1161-1163 may be lined and/or filled with an electrically conductive material (e.g., copper or silver) to provide electrical connections between layers 1101-1103. In some implementations, motor cable 1100 may a flexible ribbon cable and/or a continuous printed circuit.

As shown, electrical conduit 1111 includes portions of layers 1101-1103, input pad 1121, output pad 1131, and through holes 1151-1153 and 1161. During operation, a controller (e.g., controller 130) may provide a first signal to one or more coils (e.g., coils 244, 410-415, or 940) of an intravascular blood pump (e.g., blood pumps 110, 200, or 900) through electrical conduit 1111. Electrical conduit 1112 includes portions of layers 1101-1103, input pad 1122, output pad 1132, and through holes 1154-1156, 1162, and 1163. During operation, a controller may provide a second signal to one or more coils of an intravascular blood pump through electrical conduit 1112. Electrical conduit 1113 includes portions of layer 1101, input pad 1123, and output pad 1133. During operation, a controller may provide a third signal to one or more coils of an intravascular blood pump through electrical conduit 1113.

During assembly, input pads 1121-1123 may be coupled to a connector or soldered to an electrical conduit (e.g., a portion of plug 170) for interfacing with a controller (e.g., controller 130). Furthermore, during assembly, output pads 1131-1133 and connection pads 1141-1144 may be used to form the circuit configurations described above in relation to FIGS. 6(*a*)-(*d*). For example, in relation to circuit configuration 601, connection pads 1141-1144 may be used to form nodes 630-633 and output pads 1131-1133 may be used to form nodes 634-636. As another example, in relation to circuit configuration 602, connection pads 1141-1144 may be used to form nodes 631-633 and output pads 1131-1133 may be used to form nodes 641-643. In some such implementations, one of connection pads 1141-1144 may be unused. Alternatively, in other implementations, one of connection pads 1141-1144 may be removed from cable 1100.

In comparison to head portion 1080 of cable 1000, which has an O-shape, head portion 1180 of cable 1100 has a C-shape. In some implementations, during assembly, cable 1100 may be bent in much the same way as cable 1000. For example, cable 1100 may be bent at or near the section of tail portion 1170 between connection pads 1141 and 1144 at an angle between, for example, 45 and 135 degrees. Alternatively, during assembly, cable 1100 may be bent at or near the interface between tail portion 1170 and head portion 1180 (e.g., the section of tail portion 1170 between connection pads 1142 and 1143) at an angle between, for example, 45 and 135 degrees. Bending cable 1100 at this location may help reduce the overall width of an intravascular blood pump (e.g., blood pumps 110, 200, or 900) and/or position cable 1100 closer to a central axis of the intravascular blood pump near the connection between a motor housing (e.g., motor housing 116) and a catheter (e.g., catheter 117).

In relation to, for example, blood pump 900 of FIGS. 9(*a*) and 9(*b*), cable 1100 may replace PCB 930 and electrical conduits 951-953. For example, head portion 1180 may be viewed as replacing PCB 930 and tail portion 1170 may be viewed as replacing electrical conduits 951-953. In such implementations, head portion 1180 may be connected to bearing 910 through the use of an adhesive. For example, an adhesive layer (not shown) may be included in head portion 1180 beneath bottom layer 1103. Advantageously, this substitution reduces the amount of manual soldering required to assemble blood pump 900. For example, there is no longer a need to solder electrical conduits 951-953 to PCB 930 since tail portion 1170 and head portion 1180 are already connected to one another. Furthermore, as noted above, manually soldering coils 940 to electrical conduits 951-953 may be more difficult than manually soldering coils 940 to each other. As a result, there is an overall reduced complexity, and reduced risk of unintentionally shorting coils and/or electrical conduits. For example, eliminating the solder connection of electrical conduits 951-953 to PCB 930 reduces the risk of electrically shorting the solder joints or the electrical conduits themselves to the motor housing.

Various modifications can be made to cable 1100. For example, cable 1100 may include more or fewer pads. For example, as noted above, in order to implement circuit configuration 602, one of connection pads 1141-1144 may be removed from cable 1100. As another example, in order to implement circuit configuration 603, two additional connection pads may be added to cable 1100. As yet another example, in order to implement circuit configuration 604, three of connection pads 1141-1144 may be removed. In other implementations, cable 1100 may include more or fewer through holes. For example, additional through holes may be added to further improve or reconfigure the electrical connection between layers 1101-1103. Due to the overall size constraints of an intravascular blood pump, this may be more effective than increasing the size of through holes 1151-1156 and/or 1161-1163. For example, increasing the size of through holes 1151-1156 and/or 1161-1163 may require widening tail portion 1170. In other implementations, input pads 1121-1123, output pads 1131-1133, and/or connection pads 1141-1144 may be shaped differently. For example, each of input pads 1121-1123, output pads 1131-1133, and/or connection pads 1141-1144 may have the same size and/or shape. Similarly, in other implementations, cable 1100 may be shaped differently. For example, in implementations where a shaft (e.g., shafts 253 or 920) does not extend through a bearing (e.g., bearing 700 or 910) of an intravascular blood pump (e.g., blood pumps 110, 200, or 900), central opening 1181 may be removed from cable 1100. In such implementations, central opening 1181 may be replaced with one or more additional electrical connections (e.g., one or more additional pads). Furthermore, in such implementations, the size and/or position of output pads 1131-1133 and/or connection pads 1141-1144 may be adjusted. For example, the size of output pads 1131-1133 and/or connection pads 1141-1144 may be increased to further reduce the risk of unintentionally shorting coils (e.g., coils 244, 410-415, or 940) and/or electrical conduits 1111-1113. In other implementations, there may be more or fewer layers in cable 1100. For example, cable 1100 may include one or two conductive layers, with applicable pad and through-hole configurations, or cable 1100 may include four, five or more conductive layers, with applicable pad and through-hole configurations.

Figure 12:
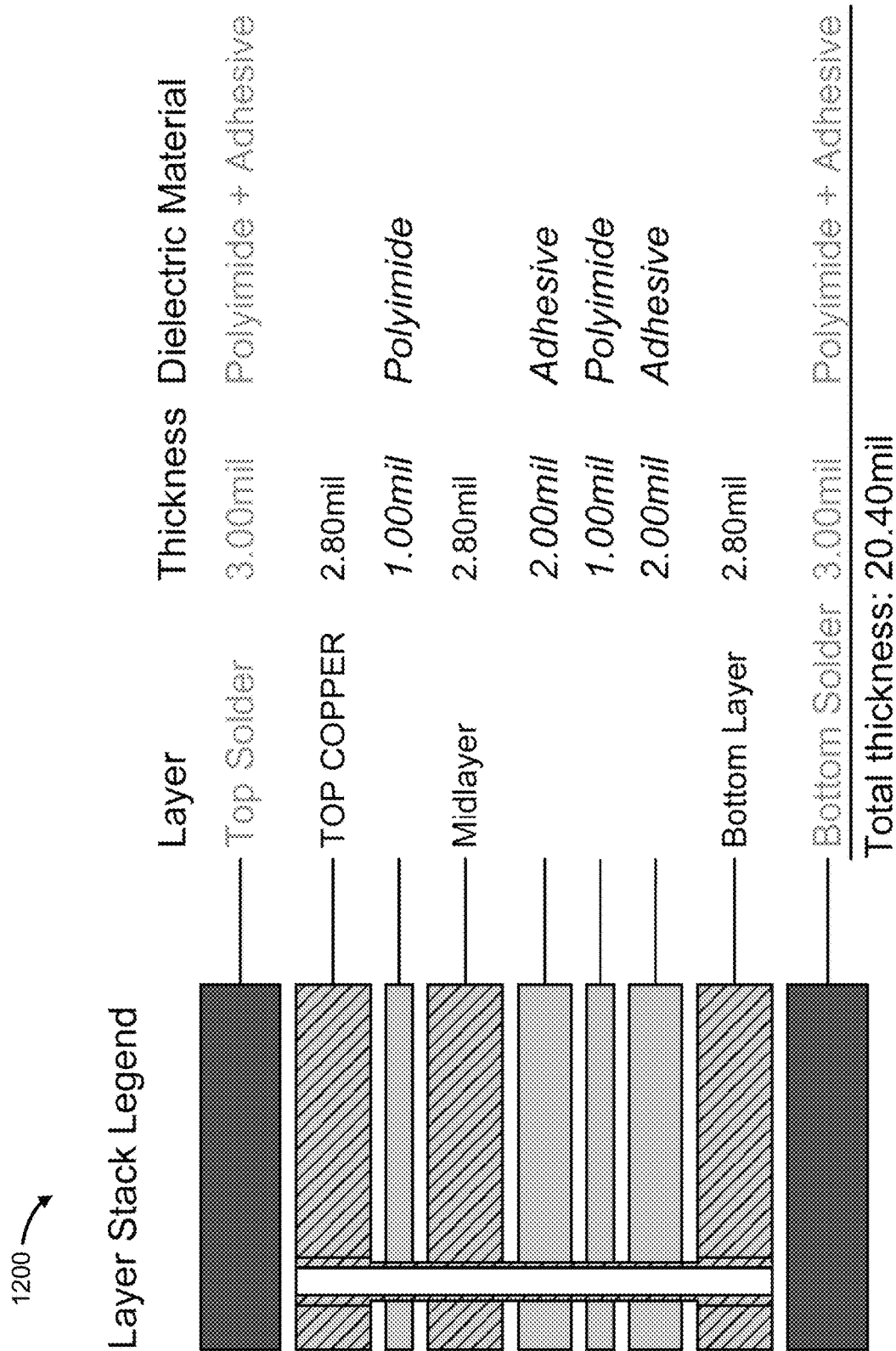
FIG. 12 illustrates an example of a layer stack legend.

FIG. 12 illustrates an example of a layer stack legend 1200 for cables 1000 and/or 1100. In such implementations, top layers 1001 and 1101, middle layers 1002 and 1102, and bottom layers 1003 and 1103 have a thickness of 2.8 millimeters. Top layers 1001 and 1101 are separated from middle layers 1002 and 1102, respectively, by a single layer of polyimide having a thickness of 1 millimeter. Middle layers 1002 and 1102 are separated from bottom layers 1003 and 1103, respectively, by a single layer of polyimide having a thickness of 1 millimeter and two layers of adhesive each having a thickness of 2 millimeters. A 3-millimeter coating of polyimide and adhesive is provided above top layers 1001 and 1101 and below bottom layers 1003 and 1103. In some implementations, the coating may not be included above input pads 1021-1023 and/or 1121-1123, output pads 1031-1033 and/or 1131-1133, and/or connection pads 1041-1044 and/or 1141-1144. Various modifications can be made to layer stack legend 1200. For example, any of the specific dimensions (e.g., thickness) can be increased or decreased. As another example, layers of polyimide and/or adhesive may be added or removed. For example, one or more polyimide and/or adhesive layers may be added between top layers 1001 and 1101 and middle layers 1002 and 1102, respectively. As another example, one or more polyimide and/or adhesive layers may be removed between middle layers 1002 and 1102 and bottom layers 1003 and 1103, respectively.

Figure 13:
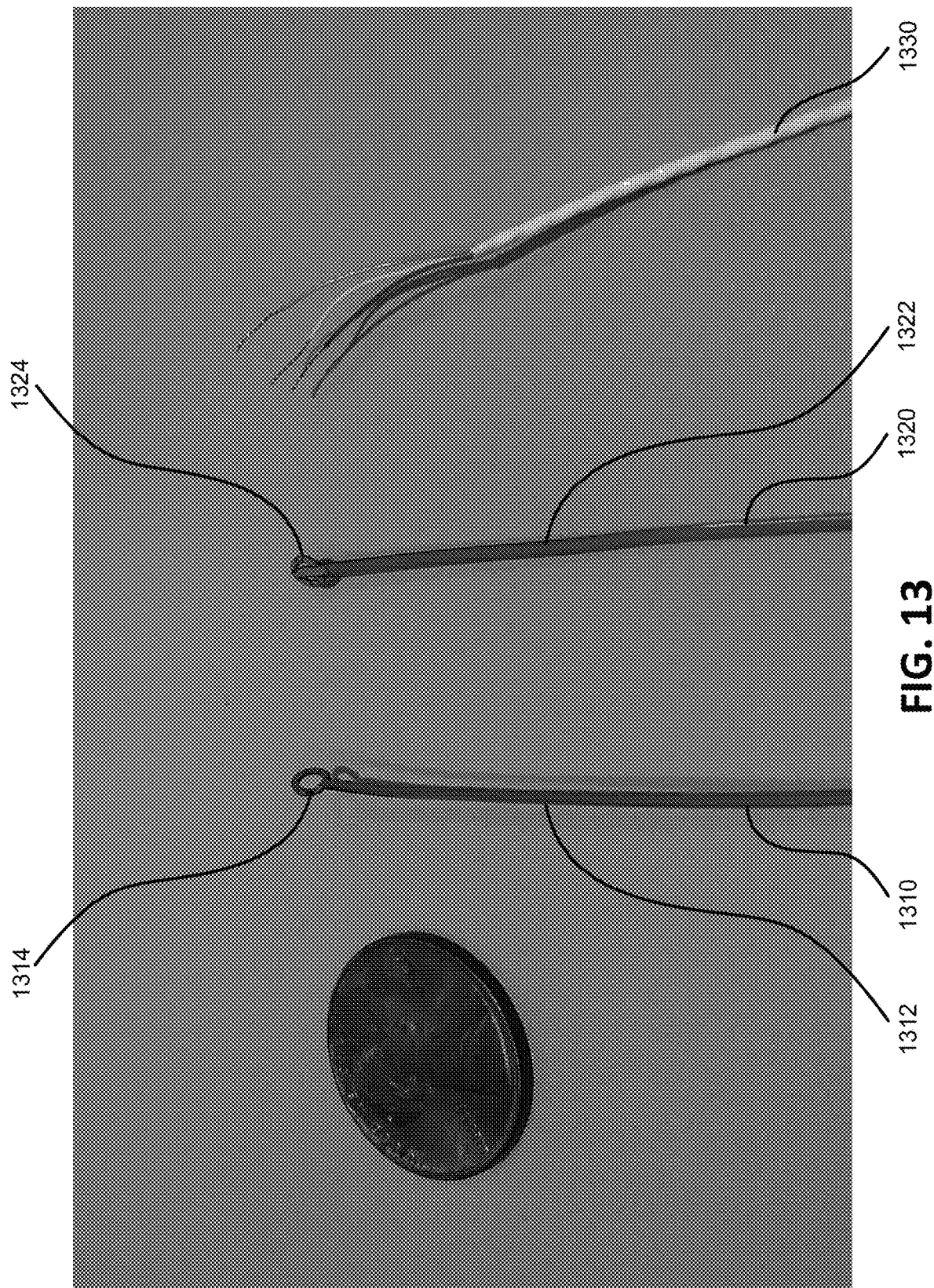
FIG. 13 is an illustration of motor cables alongside a penny.

FIG. 13 illustrates cables 1310, 1320, and 1330 alongside a penny. Cable 1310 is a prototype of cable 1000 of FIGS. 10(*a*)-(*c*). Cable 1320 is a prototype of cable 1100 of FIGS. 11(*a*)-(*c*). Cable 1330 is a motor cable having the electrical conduits 951-953 of FIGS. 9(*a*) and 9(*b*). As shown, tail portions 1312 and 1322 are covered with a coating, whereas head portions 1314 and 1324 are exposed. As shown, tail portions 1312 and 1322 have a similar width to cable 1310. Furthermore, head portions 1314 and 1324 may have a similar size to PCB 930.

From the foregoing and with reference to the various figure drawings, those skilled in the art will appreciate that certain modifications can also be made to the present disclosure without departing from the scope of the same. While several implementations of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular implementations. Those skilled in the art will envision other modifications within the scope and spirit of the claims appended hereto.

The invention claimed is:

1. An intravascular blood pump comprising:
   an inlet area having one or more openings;
   an outlet area having one or more openings;
   a passage fluidically coupling the inlet and outlet areas;
   a motor having a rotor and a stator, wherein the stator comprises one or more coils, wherein the stator is configured to generate a rotating magnetic field in response to receiving one or more electrical signals at the one or more coils, wherein the rotating magnetic field causes the rotor to rotate, and wherein rotation of the rotor draws blood into the one or more openings of the inlet area, channels the blood through the passage, and expels the blood through the one or more openings of the outlet area; and
   a cable having a tail portion and a head portion, wherein one or more electrical conduits extend through the tail and head portions, wherein the head portion comprises one or more pads, and wherein at least one of the coils is coupled to at least one of the electrical conduits through at least one of the pads.

2. The intravascular blood pump of claim 1, wherein the stator has an even number of coils.

3. The intravascular blood pump of claim 1, wherein the one or more coils and the one or more electrical conduits are coupled to the one or more pads to form a star circuit configuration.

4. The intravascular blood pump of claim 1, wherein the one or more coils and the one or more electrical conduits are coupled to the one or more pads to form a delta circuit configuration.

5. The intravascular blood pump of claim 1, wherein the one or more coils and the one or more electrical conduits are coupled to the one or more pads to form an open end windings circuit configuration.

6. The intravascular blood pump of claim 1, wherein the head portion of the cable is coupled to a yoke of the motor.

7. The intravascular blood pump of claim 1, wherein the head portion of the cable is coupled to a bearing or a bushing.

8. The intravascular blood pump of claim 7, wherein a shaft extends through (a) an opening of the bearing or the busing and (b) an opening of the head portion of the cable.

9. The intravascular blood pump of claim 1, wherein at least one of the electrical conduits comprises a plurality of electrically conductive layers and a plurality of through holes, and wherein each of the conductive layers is separated by at least one electrically insulating layer.

10. The intravascular blood pump of claim 9, wherein the head portion of the cable comprises an adhesive layer beneath the plurality of conductive layers.

11. The intravascular blood pump of claim 9, wherein the head portion is O-shaped.

12. The intravascular blood pump of claim 9, wherein the head portion is C-shaped.

13. The intravascular blood pump of claim 9, wherein the tail portion comprises a coating covering sections of the plurality of electrically conductive layers.

14. The intravascular blood pump of claim 13, wherein the tail portion comprises one or more pads, and wherein the one or more pads of the tail portion and the one or more pads of the head portion are exposed.

15. The intravascular blood pump of claim 1, wherein the cable is bent near an interface between the tail portion and the head portion at an angle between 45 and 135 degrees.

16. A method for assembling an intravascular blood pump comprising a motor and a cable, the method comprising:
   coupling a head portion of the cable to an internal structure of the intravascular blood pump, wherein the cable further comprises a tail portion, wherein one or more electrical conduits extend through the tail and head portions, and wherein the head portion comprises one or more pads; and
   coupling at least one coil of the motor to at least one of the electrical conduits through at least one of the pads, wherein the motor further comprises a rotor and a stator, wherein the stator comprises one or more coils, wherein the stator is configured to generate a rotating magnetic field in response to receiving one or more electrical signals at the one or more coils, and wherein the rotating magnetic field causes the rotor to rotate.

17. The method of claim 16, wherein the head portion is O-shaped or C-shaped.

18. The method of claim 17, wherein at least one of the electrical conduits comprises a plurality of electrically conductive layers and a plurality of through holes, and wherein each of the conductive layers is separated by at least one electrically insulating layer.

19. The method of claim 18, wherein the head portion comprises an adhesive layer beneath the plurality of conductive layers, and wherein coupling the head portion to the internal structure of the intravascular blood pump comprises placing the adhesive layer on the internal structure.

20. The method of claim 19, wherein coupling the at least one coil to the at least one of the electrical conduits through the at least one of the pads comprises soldering the at least one coil to the at least one of the pads.

* * * * *